(12) United States Patent
McBride et al.

(10) Patent No.: US 11,890,485 B2
(45) Date of Patent: Feb. 6, 2024

(54) IMPLANTABLE POWER ADAPTER

(71) Applicant: Bioness Inc., Valencia, CA (US)

(72) Inventors: Keith McBride, Ventura, CA (US); Arkady Glukhovsky, Valencia, CA (US)

(73) Assignee: Bioness Inc., Valencia, CA (US)

( * ) Notice: Subject to any disclaimer, the term of this patent is extended or adjusted under 35 U.S.C. 154(b) by 294 days.

(21) Appl. No.: 17/379,220

(22) Filed: Jul. 19, 2021

(65) Prior Publication Data

US 2021/0346704 A1   Nov. 11, 2021

Related U.S. Application Data

(62) Division of application No. 16/504,623, filed on Jul. 8, 2019, now Pat. No. 11,065,461.

(51) Int. Cl.
*A61N 1/378* (2006.01)
*A61N 1/372* (2006.01)
*A61B 5/00* (2006.01)

(52) U.S. Cl.
CPC .......... *A61N 1/378* (2013.01); *A61N 1/37211* (2013.01); *A61B 5/0031* (2013.01)

(58) Field of Classification Search
CPC .. A61N 1/378; A61N 1/37211; A61N 1/3787; A61B 5/0031
See application file for complete search history.

(56) References Cited

U.S. PATENT DOCUMENTS

| | | |
|---|---|---|
| 3,204,637 A | 9/1965 | Frank et al. |
| 3,426,748 A | 2/1969 | Bowers et al. |
| 3,494,907 A | 2/1970 | Merijan et al. |
| 3,563,968 A | 2/1971 | Merijan et al. |
| 3,796,221 A | 3/1974 | Hagfors |
| 4,269,198 A | 5/1981 | Stokes |
| 4,271,847 A | 6/1981 | Stokes |

(Continued)

FOREIGN PATENT DOCUMENTS

| | | |
|---|---|---|
| CN | 204684455 U | 10/2015 |
| CN | 109603007 A | 4/2019 |

(Continued)

OTHER PUBLICATIONS

Becerra-Fajardo et al., "In Vivo Demonstration of Addressable Microstimulators Powered by Rectification of Epidermically Applied Currents for Miniaturized Neuroprostheses," PLoS One (2015) 10(7): e0131666, 19 pages.

(Continued)

*Primary Examiner* — Mark W. Bockelman
(74) *Attorney, Agent, or Firm* — COOLEY LLP

(57) ABSTRACT

An apparatus includes a power adapter having a housing and a circuit at least partially disposed in the housing. The housing is configured to be coupled to an implantable device for disposition in a body. The circuit is configured to be electrically connected to a power circuit of the implantable device when the housing is coupled to the implantable electrical conductor. When the housing is coupled to the implantable electrical conductor and implanted in a body, the circuit is configured to (1) receive, transcutaneously from a power supply, a first energy, (2) convert the first energy to a second energy, and (3) transfer, to the implantable device, the second energy such that the second energy powers the implantable device.

27 Claims, 17 Drawing Sheets

(56) References Cited

U.S. PATENT DOCUMENTS

| | | |
|---|---|---|
| 4,479,500 A | 10/1984 | Smits |
| 4,506,673 A | 3/1985 | Bonnell |
| 4,515,167 A | 5/1985 | Hochman |
| 4,559,951 A | 12/1985 | Dahl et al. |
| 4,574,814 A | 3/1986 | Buffet |
| 4,658,835 A | 4/1987 | Pohndorf |
| 4,664,120 A | 5/1987 | Hess |
| 4,702,732 A | 10/1987 | Powers et al. |
| 4,917,104 A | 4/1990 | Rebell |
| 4,989,617 A | 2/1991 | Memberg et al. |
| 5,012,806 A | 5/1991 | De Bellis |
| 5,016,646 A | 5/1991 | Gotthardt et al. |
| 5,030,457 A | 7/1991 | Ng et al. |
| 5,217,028 A | 6/1993 | Dutcher et al. |
| 5,231,996 A | 8/1993 | Bardy et al. |
| 5,300,107 A | 4/1994 | Stokes et al. |
| 5,324,316 A | 6/1994 | Schulman et al. |
| 5,330,489 A | 7/1994 | Green et al. |
| 5,405,367 A | 4/1995 | Schulman et al. |
| 5,441,527 A | 8/1995 | Erickson et al. |
| 5,545,206 A | 8/1996 | Carson |
| 5,653,742 A | 8/1997 | Parker et al. |
| 5,769,858 A | 6/1998 | Pearson et al. |
| 5,814,090 A | 9/1998 | Latterell et al. |
| 5,849,033 A | 12/1998 | Mehmanesh et al. |
| 5,861,019 A | 1/1999 | Sun et al. |
| 5,871,531 A | 2/1999 | Struble |
| 5,897,585 A | 4/1999 | Williams |
| 5,919,222 A | 7/1999 | Hjelle et al. |
| 5,931,864 A | 8/1999 | Chastain et al. |
| 5,939,453 A | 8/1999 | Heller et al. |
| 5,944,729 A | 8/1999 | Blake |
| 5,954,759 A | 9/1999 | Swoyer et al. |
| 5,968,543 A | 10/1999 | Heller et al. |
| 6,006,122 A | 12/1999 | Smits |
| 6,083,216 A | 7/2000 | Fischer, Sr. |
| 6,153,664 A | 11/2000 | Wise et al. |
| 6,178,355 B1 | 1/2001 | Williams et al. |
| 6,178,356 B1 | 1/2001 | Chastain et al. |
| 6,181,973 B1 | 1/2001 | Ceron et al. |
| 6,214,032 B1 | 4/2001 | Loeb et al. |
| 6,240,322 B1 | 5/2001 | Peterfeso et al. |
| 6,289,251 B1 | 9/2001 | Huepenbecker et al. |
| 6,304,786 B1 | 10/2001 | Heil, Jr. et al. |
| 6,330,481 B1 | 12/2001 | Van Wijk et al. |
| 6,438,428 B1 | 8/2002 | Axelgaard et al. |
| 6,505,074 B2 | 1/2003 | Boveja et al. |
| 6,505,082 B1 | 1/2003 | Scheiner et al. |
| 6,510,347 B2 | 1/2003 | Borkan |
| 6,517,559 B1 | 2/2003 | O'Connell |
| 6,580,949 B1 | 6/2003 | Tsuboi et al. |
| 6,650,922 B2 | 11/2003 | Kurata et al. |
| 6,666,208 B1 | 12/2003 | Schumacher et al. |
| 6,735,474 B1 | 5/2004 | Loeb et al. |
| 6,735,475 B1 | 5/2004 | Whitehurst et al. |
| 6,754,472 B1 | 6/2004 | Williams et al. |
| 6,788,979 B1 | 9/2004 | Axelgaard et al. |
| 6,829,508 B2 | 12/2004 | Schulman et al. |
| 6,847,844 B2 | 1/2005 | Sun et al. |
| 6,896,675 B2 | 5/2005 | Leung et al. |
| 6,909,918 B2 | 6/2005 | Stypulkowski |
| 6,913,765 B2 | 7/2005 | Li et al. |
| 6,925,318 B2 | 8/2005 | Bencini |
| 6,939,569 B1 | 9/2005 | Green et al. |
| 6,941,171 B2 | 9/2005 | Mann et al. |
| 6,961,623 B2 | 11/2005 | Prochazka |
| 6,997,735 B2 | 2/2006 | Ehr et al. |
| 6,999,819 B2 | 2/2006 | Swoyer et al. |
| 7,004,948 B1 | 2/2006 | Pianca et al. |
| 7,013,179 B2 | 3/2006 | Carter et al. |
| 7,043,299 B2 | 5/2006 | Erlinger et al. |
| 7,058,456 B2 | 6/2006 | Pierce |
| 7,062,330 B1 | 6/2006 | Boveja et al. |
| 7,101,394 B2 | 9/2006 | Hamm et al. |
| 7,101,840 B2 | 9/2006 | Brocchini et al. |
| 7,146,222 B2 | 12/2006 | Boling |
| 7,155,292 B2 | 12/2006 | Kawula et al. |
| 7,162,303 B2 | 1/2007 | Levin et al. |
| 7,187,980 B2 | 3/2007 | Osypka et al. |
| 7,191,018 B2 | 3/2007 | Gielen et al. |
| 7,210,210 B2 | 5/2007 | Lippitt et al. |
| 7,212,869 B2 | 5/2007 | Wahlstrom et al. |
| 7,324,853 B2 | 1/2008 | Ayal et al. |
| 7,349,742 B2 | 3/2008 | Heil et al. |
| 7,389,145 B2 | 6/2008 | Kilgore et al. |
| 7,502,652 B2 | 3/2009 | Gaunt et al. |
| 7,536,226 B2 | 5/2009 | Williams et al. |
| 8,025,668 B2 | 9/2011 | McCartney |
| 8,027,718 B2 | 9/2011 | Spinner et al. |
| 8,032,220 B2 | 10/2011 | Kuzma |
| 8,170,675 B2 | 5/2012 | Alataris et al. |
| 8,209,021 B2 | 6/2012 | Alataris et al. |
| 8,255,057 B2 | 8/2012 | Fang et al. |
| 8,332,029 B2 | 12/2012 | Glukhovsky et al. |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,361,067 B2 | 1/2013 | Pellegrino et al. |
| 8,396,559 B2 | 3/2013 | Alataris et al. |
| 8,406,886 B2 | 3/2013 | Gaunt et al. |
| 8,414,571 B2 | 4/2013 | Pellegrino et al. |
| 8,419,730 B2 | 4/2013 | Pellegrino et al. |
| 8,419,731 B2 | 4/2013 | Pellegrino et al. |
| 8,423,147 B2 | 4/2013 | Alataris et al. |
| 8,425,507 B2 | 4/2013 | Pellegrino et al. |
| 8,428,728 B2 | 4/2013 | Sachs |
| 8,428,748 B2 | 4/2013 | Alataris et al. |
| 8,509,905 B2 | 8/2013 | Alataris et al. |
| 8,509,906 B2 | 8/2013 | Walker et al. |
| 8,535,309 B2 | 9/2013 | Pellegrino et al. |
| 8,538,517 B2 | 9/2013 | Glukhovsky et al. |
| 8,554,326 B2 | 10/2013 | Alataris et al. |
| 8,583,256 B2 | 11/2013 | Tracey et al. |
| 8,588,930 B2 | 11/2013 | Diubaldi et al. |
| 8,613,744 B2 | 12/2013 | Pellegrino et al. |
| 8,623,014 B2 | 1/2014 | Pellegrino et al. |
| 8,628,528 B2 | 1/2014 | Pellegrino et al. |
| 8,649,874 B2 | 2/2014 | Alataris et al. |
| 8,676,331 B2 | 3/2014 | Parker |
| 8,694,108 B2 | 4/2014 | Alataris et al. |
| 8,694,109 B2 | 4/2014 | Alataris et al. |
| 8,706,230 B2 | 4/2014 | Rousso et al. |
| 8,712,533 B2 | 4/2014 | Alataris et al. |
| 8,718,781 B2 | 5/2014 | Alataris et al. |
| 8,718,782 B2 | 5/2014 | Alataris et al. |
| 8,751,003 B2 | 6/2014 | Diubaldi et al. |
| 8,768,472 B2 | 7/2014 | Fang et al. |
| 8,774,926 B2 | 7/2014 | Alataris et al. |
| 8,792,988 B2 | 7/2014 | Alataris et al. |
| 8,798,754 B2 | 8/2014 | Knudson et al. |
| 8,805,519 B2 | 8/2014 | Parker et al. |
| 8,808,284 B2 | 8/2014 | Pellegrino et al. |
| 8,838,248 B2 | 9/2014 | Walker et al. |
| 8,843,188 B2 | 9/2014 | Kilgore et al. |
| 8,849,410 B2 | 9/2014 | Walker et al. |
| 8,862,225 B2 | 10/2014 | Glukhovsky et al. |
| 8,862,239 B2 | 10/2014 | Alataris et al. |
| 8,868,192 B2 | 10/2014 | Alataris et al. |
| 8,874,217 B2 | 10/2014 | Alataris et al. |
| 8,874,221 B2 | 10/2014 | Alataris et al. |
| 8,874,222 B2 | 10/2014 | Alataris et al. |
| 8,880,177 B2 | 11/2014 | Alataris et al. |
| 8,880,189 B2 | 11/2014 | Lipani |
| 8,882,764 B2 | 11/2014 | Sutton et al. |
| 8,886,326 B2 | 11/2014 | Alataris et al. |
| 8,886,327 B2 | 11/2014 | Alataris et al. |
| 8,886,328 B2 | 11/2014 | Alataris et al. |
| 8,892,209 B2 | 11/2014 | Alataris et al. |
| 8,903,494 B2 | 12/2014 | Goldwasser et al. |
| 8,903,502 B2 | 12/2014 | Perryman et al. |
| 8,918,181 B2 | 12/2014 | Ackermann et al. |
| 8,958,880 B2 | 2/2015 | DeGiorgio et al. |
| 8,965,482 B2 | 2/2015 | Thacker et al. |
| 8,989,865 B2 | 3/2015 | Alataris et al. |

(56) References Cited

U.S. PATENT DOCUMENTS

| | | |
|---|---|---|
| 8,992,522 B2 | 3/2015 | Pellegrino et al. |
| 8,992,523 B2 | 3/2015 | Pellegrino et al. |
| 8,996,137 B2 | 3/2015 | Ackermann et al. |
| 9,002,458 B2 | 4/2015 | Pal et al. |
| 9,002,460 B2 | 4/2015 | Parker |
| 9,002,467 B2 | 4/2015 | Smith et al. |
| 9,014,811 B2 | 4/2015 | Pal et al. |
| 9,017,325 B2 | 4/2015 | Pellegrino et al. |
| 9,023,038 B2 | 5/2015 | Pellegrino et al. |
| 9,039,701 B2 | 5/2015 | Pellegrino et al. |
| 9,072,886 B2 | 7/2015 | Gaunt et al. |
| 9,095,723 B2 | 8/2015 | Ackermann et al. |
| 9,101,769 B2 | 8/2015 | Edgerton et al. |
| 9,173,676 B2 | 11/2015 | Pellegrino et al. |
| 9,174,006 B2 | 11/2015 | Vosseler et al. |
| 9,180,298 B2 | 11/2015 | Alataris et al. |
| 9,220,897 B2 | 12/2015 | Perryman et al. |
| 9,233,244 B2 | 1/2016 | Pal et al. |
| 9,238,139 B2 | 1/2016 | DeGiorgio et al. |
| 9,242,113 B2 | 1/2016 | Smith et al. |
| 9,248,278 B2 | 2/2016 | Crosby et al. |
| 9,248,293 B2 | 2/2016 | Walker et al. |
| 9,259,241 B2 | 2/2016 | Pellegrino et al. |
| 9,265,522 B2 | 2/2016 | Pellegrino et al. |
| 9,265,956 B2 | 2/2016 | Ackermann et al. |
| 9,278,215 B2 | 3/2016 | Thacker et al. |
| 9,283,387 B2 | 3/2016 | Thacker et al. |
| 9,283,388 B2 | 3/2016 | Thacker et al. |
| 9,295,839 B2 | 3/2016 | Thacker et al. |
| 9,327,121 B2 | 5/2016 | Thacker et al. |
| 9,327,125 B2 | 5/2016 | Alataris et al. |
| 9,327,126 B2 | 5/2016 | Alataris et al. |
| 9,327,127 B2 | 5/2016 | Alataris et al. |
| 9,333,357 B2 | 5/2016 | Alataris et al. |
| 9,333,358 B2 | 5/2016 | Alataris et al. |
| 9,333,359 B2 | 5/2016 | Alataris et al. |
| 9,333,360 B2 | 5/2016 | Alataris et al. |
| 9,345,891 B2 | 5/2016 | Thacker et al. |
| 9,352,164 B2 | 5/2016 | Smith et al. |
| 9,358,388 B2 | 6/2016 | Parker et al. |
| 9,364,661 B2 | 6/2016 | Kilgore et al. |
| 9,364,674 B2 | 6/2016 | Cook et al. |
| 9,387,327 B2 | 7/2016 | Alataris et al. |
| 9,393,409 B2 | 7/2016 | Edgerton et al. |
| 9,393,430 B2 | 7/2016 | Demers et al. |
| 9,399,126 B2 | 7/2016 | Pal et al. |
| 9,403,011 B2 | 8/2016 | Mercanzini |
| 9,403,013 B2 | 8/2016 | Walker et al. |
| 9,403,020 B2 | 8/2016 | Wingeier |
| 9,409,011 B2 | 8/2016 | Tai et al. |
| 9,409,019 B2 | 8/2016 | Walker et al. |
| 9,409,023 B2 | 8/2016 | Burdick et al. |
| 9,415,218 B2 | 8/2016 | Edgerton et al. |
| 9,421,064 B2 | 8/2016 | Pellegrino et al. |
| 9,440,065 B2 | 9/2016 | Ackermann et al. |
| 9,440,070 B2 | 9/2016 | Goldwasser et al. |
| 9,457,186 B2 | 10/2016 | Gross |
| 9,474,891 B2 | 10/2016 | Demers et al. |
| 9,480,842 B2 | 11/2016 | Alataris et al. |
| 9,486,279 B2 | 11/2016 | Pellegrino et al. |
| 9,504,827 B2 | 11/2016 | DeGiorgio et al. |
| 9,511,223 B2 | 12/2016 | DeGiorgio et al. |
| 9,511,226 B2 | 12/2016 | Pelizzone et al. |
| 9,517,351 B2 | 12/2016 | Charlesworth et al. |
| 9,526,909 B2 | 12/2016 | Stahmann et al. |
| 9,592,388 B2 | 3/2017 | Parker et al. |
| 9,592,391 B2 | 3/2017 | Stahmann et al. |
| 9,597,521 B2 | 3/2017 | Plotkin et al. |
| 9,604,059 B2 | 3/2017 | Parker |
| RE46,356 E | 4/2017 | Pellegrino et al. |
| 9,643,022 B2 | 5/2017 | Mashiach et al. |
| 9,669,230 B2 | 6/2017 | Koop |
| 9,682,236 B2 | 6/2017 | DeGiorgio et al. |
| 9,687,652 B2 | 6/2017 | Franke et al. |
| 9,694,189 B2 | 7/2017 | Maile et al. |
| 9,713,707 B2 | 7/2017 | Oron et al. |
| 9,717,627 B2 | 8/2017 | Kuzma et al. |
| 9,724,107 B2 | 8/2017 | Pellegrino et al. |
| 9,724,151 B2 | 8/2017 | Edidin |
| 9,737,702 B2 | 8/2017 | Ackermann et al. |
| 9,737,712 B2 | 8/2017 | Franke et al. |
| 9,757,554 B2 | 9/2017 | Dar et al. |
| 9,757,570 B2 | 9/2017 | Maile et al. |
| 9,764,146 B2 | 9/2017 | Oron et al. |
| 9,764,150 B2 | 9/2017 | Loudin et al. |
| 9,770,583 B2 | 9/2017 | Gupta et al. |
| 9,775,627 B2 | 10/2017 | Patel et al. |
| 9,789,314 B2 | 10/2017 | Perryman et al. |
| 9,808,631 B2 | 11/2017 | Maile et al. |
| 9,821,159 B2 | 11/2017 | Ackermann et al. |
| 9,833,614 B1 | 12/2017 | Gliner |
| 9,848,944 B2 | 12/2017 | Sutton et al. |
| 9,849,289 B2 | 12/2017 | Mashiach et al. |
| 9,853,743 B2 | 12/2017 | Schmidt et al. |
| 9,855,032 B2 | 1/2018 | Mashiach et al. |
| 9,861,812 B2 | 1/2018 | Gross et al. |
| 9,895,539 B1 | 2/2018 | Heit et al. |
| 9,907,950 B1 | 3/2018 | Perryman et al. |
| 9,907,958 B2 | 3/2018 | Edgerton et al. |
| 9,931,508 B2 | 4/2018 | Burdick et al. |
| 9,943,686 B2 | 4/2018 | Mashiach |
| 9,950,166 B2 | 4/2018 | Mashiach et al. |
| 9,956,397 B2 | 5/2018 | Loudin et al. |
| 9,956,405 B2 | 5/2018 | Goldwasser et al. |
| 9,956,414 B2 | 5/2018 | Kane et al. |
| 9,968,780 B2 | 5/2018 | Pal et al. |
| 9,968,783 B2 | 5/2018 | Bullinga et al. |
| 9,968,787 B2 | 5/2018 | Kane et al. |
| 9,993,642 B2 | 6/2018 | Gerasimenko et al. |
| 9,993,645 B2 | 6/2018 | Walker et al. |
| 9,993,654 B2 | 6/2018 | Smith et al. |
| 10,004,896 B2 | 6/2018 | Oron et al. |
| 10,016,600 B2 | 7/2018 | Creasey et al. |
| 10,016,601 B2 | 7/2018 | Cook et al. |
| 10,028,753 B2 | 7/2018 | Pellegrino et al. |
| 10,029,107 B1 | 7/2018 | Webb et al. |
| 10,039,917 B2 | 8/2018 | Kilgore et al. |
| 10,046,167 B2 | 8/2018 | Schmidt et al. |
| 10,050,700 B2 | 8/2018 | Ludwig et al. |
| 10,052,097 B2 | 8/2018 | Mashiach et al. |
| 10,058,704 B2 | 8/2018 | Degiorgio et al. |
| 10,065,041 B2 | 9/2018 | Huelskamp et al. |
| 10,071,241 B2 | 9/2018 | Bhadra et al. |
| 10,076,665 B2 | 9/2018 | Parker |
| 10,092,750 B2 | 10/2018 | Edgerton et al. |
| 10,092,760 B2 | 10/2018 | Kane et al. |
| 10,105,540 B2 | 10/2018 | Oron et al. |
| 10,111,704 B2 | 10/2018 | Pellegrino et al. |
| 10,112,048 B2 | 10/2018 | Franke et al. |
| 10,124,166 B2 | 11/2018 | Edgerton et al. |
| 10,124,178 B2 | 11/2018 | Oron et al. |
| 10,137,299 B2 | 11/2018 | Lu et al. |
| 10,137,305 B2 | 11/2018 | Kane et al. |
| 10,143,846 B2 | 12/2018 | Ackermann et al. |
| 10,149,978 B1 | 12/2018 | Park |
| 10,155,108 B2 | 12/2018 | Ackermann et al. |
| 10,159,842 B2 | 12/2018 | Kane et al. |
| 10,173,065 B2 | 1/2019 | Walker et al. |
| 10,179,241 B2 | 1/2019 | Walker et al. |
| 10,179,244 B2 | 1/2019 | LeBaron et al. |
| 10,183,170 B2 | 1/2019 | Kane et al. |
| 10,195,433 B2 | 2/2019 | Alataris et al. |
| 10,195,434 B2 | 2/2019 | Bhadra et al. |
| 10,195,435 B2 | 2/2019 | Degiorgio et al. |
| 10,207,108 B2 | 2/2019 | Franke et al. |
| 10,213,610 B2 | 2/2019 | Maile et al. |
| 10,220,208 B2 | 3/2019 | Alataris et al. |
| 10,220,209 B2 | 3/2019 | Alataris et al. |
| 10,220,213 B2 | 3/2019 | Huelskamp et al. |
| 10,226,626 B2 | 3/2019 | Alataris et al. |
| 10,226,631 B2 | 3/2019 | Kane et al. |
| 10,238,861 B2 | 3/2019 | Ackermann et al. |
| 10,238,862 B2 | 3/2019 | Cook et al. |
| 10,238,863 B2 | 3/2019 | Gross et al. |

(56) References Cited

U.S. PATENT DOCUMENTS

| | | | |
|---|---|---|---|
| 10,238,872 | B2 | 3/2019 | Pivonka et al. |
| 10,238,874 | B2 | 3/2019 | Perryman et al. |
| 10,238,882 | B2 | 3/2019 | Koop |
| 10,245,433 | B2 | 4/2019 | Alataris et al. |
| 10,252,048 | B2 | 4/2019 | Loudin et al. |
| 10,369,369 | B2 | 8/2019 | Perryman et al. |
| 10,485,980 | B2 | 11/2019 | Yeh et al. |
| 11,065,461 | B2 | 7/2021 | McBride et al. |
| 2001/0051807 | A1 | 12/2001 | Grafton |
| 2002/0007204 | A1 | 1/2002 | Goode |
| 2003/0050672 | A1 | 3/2003 | Dahlberg |
| 2003/0078618 | A1 | 4/2003 | Fey et al. |
| 2003/0139794 | A1 | 7/2003 | Jenney et al. |
| 2003/0149468 | A1 | 8/2003 | Wallsten |
| 2004/0143240 | A1 | 7/2004 | Armstrong et al. |
| 2004/0164783 | A1 | 8/2004 | Baru |
| 2004/0220665 | A1 | 11/2004 | Hossainy et al. |
| 2005/0015048 | A1 | 1/2005 | Chiu et al. |
| 2005/0112759 | A1 | 5/2005 | Radisic et al. |
| 2005/0165465 | A1 | 7/2005 | Pianca et al. |
| 2005/0182449 | A1 | 8/2005 | Auge, II et al. |
| 2005/0267555 | A1 | 12/2005 | Marnfeldt et al. |
| 2005/0267557 | A1 | 12/2005 | Flynn et al. |
| 2005/0283202 | A1 | 12/2005 | Gellman |
| 2006/0058598 | A1 | 3/2006 | Esposito |
| 2006/0095078 | A1 | 5/2006 | Tronnes |
| 2006/0121180 | A1 | 6/2006 | Gertner et al. |
| 2006/0129216 | A1 | 6/2006 | Hastings et al. |
| 2006/0282123 | A1 | 12/2006 | Hunter et al. |
| 2007/0043410 | A1 | 2/2007 | Boling |
| 2007/0100411 | A1 | 5/2007 | Bonde |
| 2007/0142890 | A1 | 6/2007 | Zarembo et al. |
| 2007/0261115 | A1 | 11/2007 | Gerber et al. |
| 2007/0299491 | A1 | 12/2007 | Borgaonkar et al. |
| 2008/0071340 | A1 | 3/2008 | Atanasoska et al. |
| 2009/0043367 | A1 | 2/2009 | Zilberman et al. |
| 2009/0099612 | A1 | 4/2009 | Armstrong |
| 2009/0210040 | A1 | 8/2009 | Ochoa |
| 2009/0259280 | A1 | 10/2009 | Wilkin et al. |
| 2009/0281409 | A1 | 11/2009 | Walter |
| 2009/0326611 | A1 | 12/2009 | Gillbe |
| 2010/0198298 | A1 | 8/2010 | Glukhovsky et al. |
| 2011/0282414 | A1 | 11/2011 | Kothandaraman et al. |
| 2012/0232615 | A1 | 9/2012 | Barolat et al. |
| 2013/0188397 | A1 | 7/2013 | Wu et al. |
| 2013/0274829 | A1 | 10/2013 | Gupta et al. |
| 2013/0282070 | A1 | 10/2013 | Cowan et al. |
| 2014/0074186 | A1 | 3/2014 | Faltys et al. |
| 2015/0148878 | A1 | 5/2015 | Yoo et al. |
| 2015/0165186 | A1 | 6/2015 | Dar et al. |
| 2015/0174418 | A1 | 6/2015 | Tyler et al. |
| 2015/0328462 | A1 | 11/2015 | Griffith |
| 2015/0335888 | A1 | 11/2015 | Demers et al. |
| 2016/0121115 | A1 | 5/2016 | Guillory et al. |
| 2016/0175585 | A1 | 6/2016 | Gregory et al. |
| 2016/0346530 | A1 | 12/2016 | Jeffery et al. |
| 2016/0346545 | A1 | 12/2016 | Pal et al. |
| 2016/0361535 | A1 | 12/2016 | Perryman et al. |
| 2017/0076414 | A1 | 3/2017 | Egnal et al. |
| 2017/0182285 | A1 | 6/2017 | Tyler et al. |
| 2017/0224990 | A1 | 8/2017 | Goldwasser et al. |
| 2017/0368297 | A1 | 12/2017 | Tyler et al. |
| 2018/0028824 | A1 | 2/2018 | Pivonka et al. |
| 2018/0085593 | A1 | 3/2018 | Fayram et al. |
| 2018/0256906 | A1 | 9/2018 | Pivonka et al. |
| 2018/0272118 | A1 | 9/2018 | Goldwasser et al. |
| 2018/0280708 | A1 | 10/2018 | Escalona et al. |
| 2019/0051988 | A1 | 2/2019 | Bern |
| 2019/0151659 | A1 | 5/2019 | Mishra et al. |
| 2019/0374776 | A1 | 12/2019 | Mishra et al. |
| 2020/0139138 | A1 | 5/2020 | Sit et al. |
| 2020/0197710 | A1 | 6/2020 | Harding et al. |
| 2020/0306528 | A1 | 10/2020 | Linden et al. |
| 2021/0008376 | A1 | 1/2021 | McBride et al. |

FOREIGN PATENT DOCUMENTS

| | | |
|---|---|---|
| CN | 111420281 A | 7/2020 |
| EP | 0862925 A2 | 9/1998 |
| EP | 1981589 B1 | 4/2016 |
| EP | 3449814 A1 | 3/2019 |
| GB | 2397233 A | 7/2004 |
| KR | 101653889 B1 | 9/2016 |
| WO | WO-9848887 A1 | 11/1998 |
| WO | WO-2005070494 A1 | 8/2005 |
| WO | WO-2014093288 A1 | 6/2014 |
| WO | WO-2015079319 A1 | 6/2015 |
| WO | WO-2015183620 A2 | 12/2015 |
| WO | WO-2016111974 A1 | 7/2016 |
| WO | WO-2017041138 A1 | 3/2017 |
| WO | WO-2021007340 A1 | 1/2021 |

OTHER PUBLICATIONS

"BioGlue Surgical Adhesive," [online] CryoLife, Inc., [Retrieved on Jul. 10, 2008] Retrieved from the Internet: URL: http://www.cryolife.com/products/bioglue-surgical-adhesive, 2 pages.

Bocan et al., "Adaptive Transcutaneous Power Transfer to Implantable Devices: A State of the Art Review." Sensors, vol. 16, 393 (2016), 23 pages.

Bossetti Design and Evaluation of a Transcutaneous Energy Transfer System, Department of Biomedical Engineering, Duke University, 2009, 188 pages.

Brazel et al. "Modeling of Drug Release from Swellable Polymers" European Journal of Pharmaceutics and Biopharmaceutics, vol. 49 (2000) pp. 47-58.

Brem et al., "Biocompatibility of a Biodegradable, Controlled-Release Polymer in the Rabbit Brain" Selective Cancer Therapeutics vol. 5, No. 2 (1989), pp. 55-65.

Brem et al., "Interstitial chemotherapy with drug polymer implants for the treatment of recurrent gliomas" J. Neurosurg. vol. 74, (Mar. 1991), pp. 441-446.

Brown et al., "Controlled Release of Insulin From Polymer Matrices: Control of Diabetes in Rats" Diabetes, vol. 35, (Jun. 1986), pp. 692-697.

Chamberlin et al., "Analysis of the Charge Exchange Between the Human Body and Ground: Evaluation of 'Earthing' From an Electrical Perspective," Journal of Chiropractic Medicine, vol. 13 (2014), pp. 239-246.

Chizmadzhev et al., "Electrical Properties of Skin at Medium Voltages: Contribution of Appendageal Macropores," Biophysical Journal, vol. 74 (Feb. 1998), pp. 843-856.

Cosendai et al., "Magnetic Resonance Safety and RF Bion® Microstimulators," 8th Annual Conference of the International Functional Electrical Stimulation Society (IFESS), Jul. 1-5, 2003, 3 pages.

Davis et al., "Surgical Technique to insert and retrieve BIONs® (microstimulators) safely near deep Nerves for Functional Electrical Stimulation," 7th Annual Conference of the International Functional Electrical Stimulation Society (IFESS), May 24, 2002, 3 pages.

Deer et al., "Spinal Cord Stimulation for Refractory Angina Pectoris and Peripheral Vascular Disease," Pain Physician, (2006); 9(4): 347-352.

Gabriel "Compilation of the Dielectric Properties of Body Tissues at RF and Microwave Frequencies," Final Technical Report for the Period Sep. 15, 1993 to Dec. 14, 1995 for the AFOSR/NL Bolling AFB DC 20332-0001, Feb. 1996, 271 pages.

Gabriel "Compilation of the Dielectric Properties of Body Tissues at RF and Microwave Frequencies," Final Technical Report for the Period Dec. 15, 1994 to Dec. 14, 1995 for the Armstrong Laboratory (AFMC) Brooks AFB TX 78235, Jun. 1996, 273 pages.

Gabriel "Compilation of the Dielectric Properties of Body Tissues at RF and Microwave Frequencies," Final Technical Report for the Period Sep. 15, 1993 to Dec. 14, 1994, for the Armstrong Laboratory (AFMC) Brooks AFB TX 78235, Jan. 1996, 21 pages.

Gan et al., "The Stimulus Router: A Novel Means of Directing Current From Surface Electrodes to Nerves." 10th Annual Conference of the International FES Society, Jul. 2005, pp. 21-23.

(56) References Cited

OTHER PUBLICATIONS

Goodson, "Dental Applications," Medical Applications of Controlled Release, vol. 2, Chapter 6, 1984, pp. 115-138.

International Search Report and Written Opinion of the International Searching Authority for International Application No. PCT/US2020/041234 dated Oct. 1, 2020, 13 pages.

Ivorra et al., "Flexible Thread-like Electrical Stimulation Implants Based on Rectification of Epidermically Applied Currents Which Perform Charge Balance." Replace, Repair, Restore, Relieve—Bridging Clinical and Engineering Solutions in Neurorehabilitation SE-67 (2014), pp. 447-455.

Karpul et al., "Low-power Transcutaneous Current Stimulator for Wearable Applications." BioMedical Engineering OnLine (2017) 16: pp. 1-13.

Kwon et al., "Electrically Erodible Polymer Gel for Controlled Release of Drugs," Nature, vol. 354, Nov. 28, 1991, pp. 291-293.

Langer et al., "Polymers for the Sustained Release of Proteins and other Macromolecules" Nature. Oct. 28, 1976; 263(5580): 797-800.

Levy et al., "Inhibition of Calcification of Bioprosthetic Heart Valves by Local Controlled-Release Diphosphonate". Science. Apr. 12, 1985; 228(4696): 190-2.

Liu et al., "Five Valuable Functions of Blocking Capacitors in Stimulators." 13th Annual International Conference of the FES Society (IFESS 2008), pp. 322-324.

Masters et al., "Prolonged Regional Nerve Blockade by Controlled Release of Local Anesthetic from a Biodegradable Polymer Matrix" Anesthesiology. Aug. 1, 1993; 79(2): 340-6.

Masters et al., "Sustained Local Anesthetic Release from Bioerodible Polymer Matrices: A Potential Method for Prolonged Regional Anesthesia" Pharmaceutical research. Oct. 1993; 10: 1527-32.

Narasimhan et al., "Release Kinetics, Data Interpretation," Encyclopedia of Controlled Drug Delivery, vol. 2, New York (1999), 17 pages.

Nash "Controlled Release Systems for Contraception." In R. Langer and D. Wise (eds.) Medical Applications of Controlled Release, vol. II Applications and Evaluation, CRC Press, Boca Rotan, FL (1984), pp. 35-64.

Palti "Stimulation of muscles and nerves by means of externally applied electrodes," Bulletin of the Research Council of Israel, Section E: Experimental Medicine, Jun. 1962, 10E(1): 54-56.

Park et al., "Design and Implementation of Wireless Transcutaneous Electrical Nerve Stimulator (TENS) for Smart Phone." IEICE Electronics Express, vol. 6, No. 22 (2009), pp. 1587-1594.

Pless et al., "Tumor treating fields: concept, evidence and future," Expert Opinion on Investigational Drugs, (2011) 20:8, 1099-1106.

Prochazka "Functional Microstimulation of the Lumbosacral Spinal Cord" Neural Prosthesis Program Meeting, NIH Meeting, Nov. 2004, 5 pages.

Shaikhutdinov et al., "Surface Properties of Polyacid-Poly (N-Vinyl Pyrrolidone) Complexes," Colloid Journal. Nov. 2001; 63: 779-83.

Sharon et al., "Development of Drug Delivery Systems for Use in Treatment of Narcotic Addiction" In R. E. Willette and G. Barnett (eds.), Naltrexone: Research Monograph 28, National Institute on Drug Abuse (1980) pp. 194-213.

Taalla et al., "A Review on Miniaturized Ultrasonic Wireless Power Transfer to Implantable Medical Devices," IEEE Access, Jan. 7, 2019, vol. 7, pp. 2092-2106.

Trafton "Researchers Develop a Wireless Way to Power Human Implants," SciTechDaily, Jun. 4, 2018, 4 pages, retrieved from https://scitechdaily.com/researchers-develop-wireless-way-to-power-human-implants/.

Vargas Luna et al., "Dynamic Impedance Model of the Skin-Electrode Interface for Transcutaneous Electrical Stimulation." PLoS One 10(5): e0125609 (May 2015), 15 pages.

Voigt et al., "Cathodic-leading Pulses are More Effective Than Anodic-leading Pulses in Intracortical Microstimulation of the Auditory Cortex." Journal of Neural Engineering. Mar. 19, 2019; 16(3), 15 pages.

Yolles et al., "Sustained Delivery of Drugs From Polymer/Drug Mixtures" Polymer News. 1971; 1(4-5): 9-15.

Supplementary European Search Report for European Patent Application 20837675.6, dated Nov. 9, 2023, 7 pages.

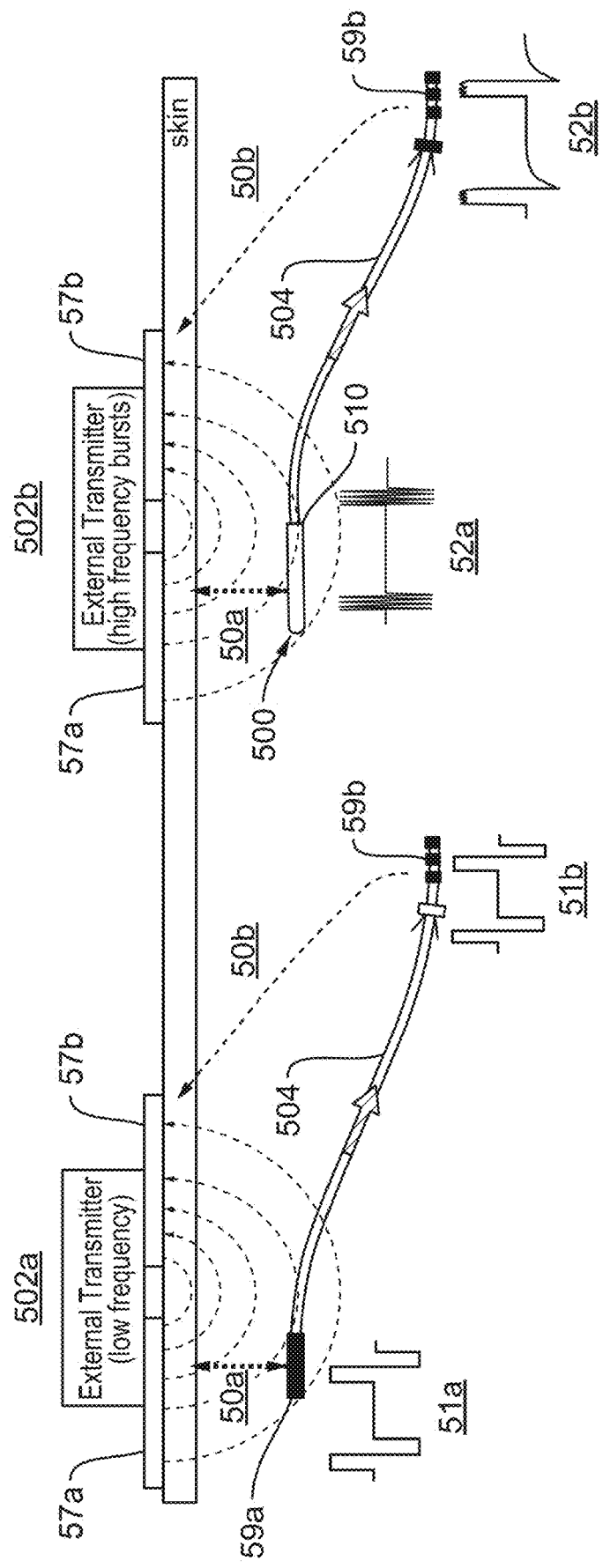

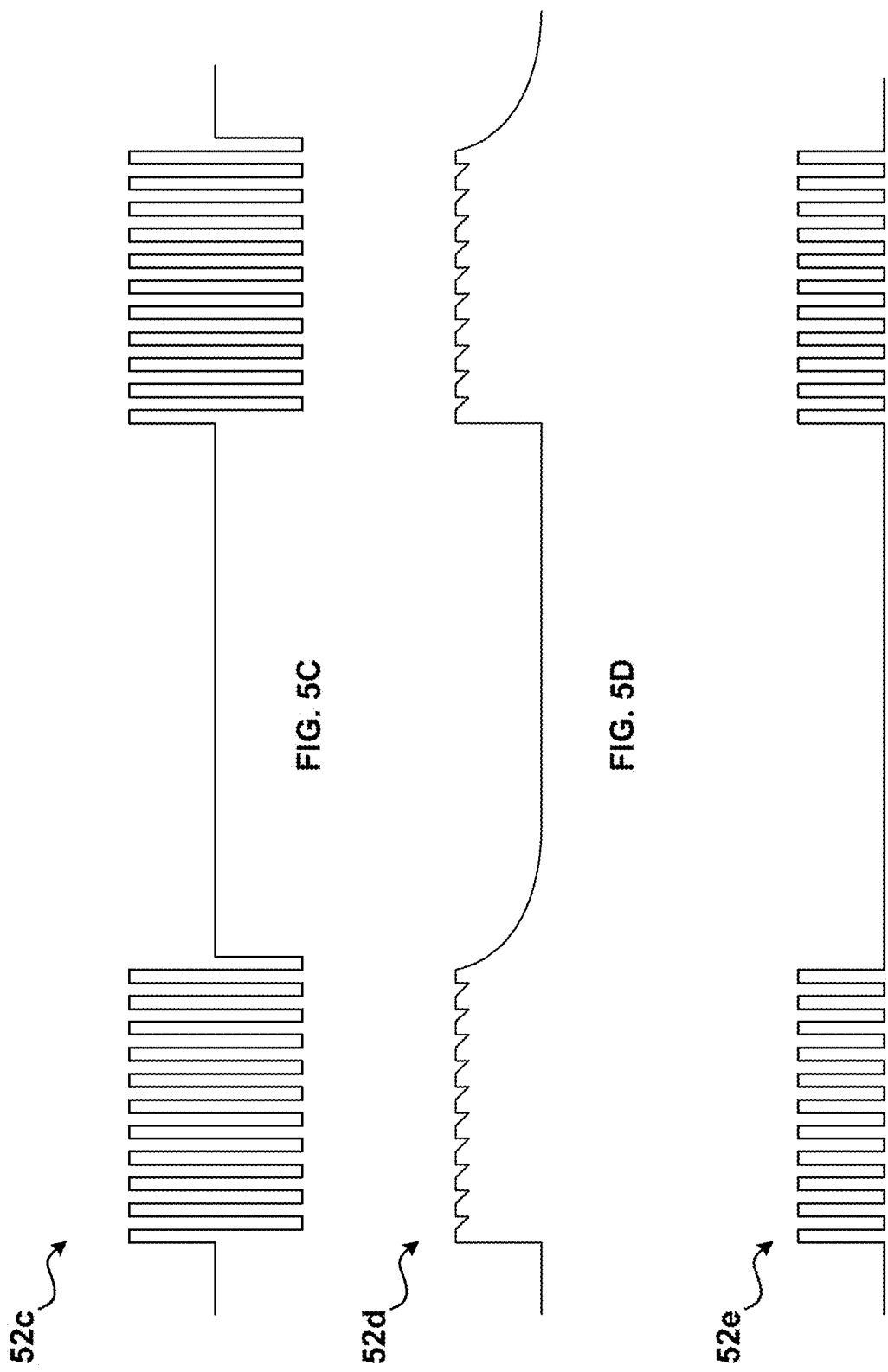

1021A

1021B

IMPLANTABLE POWER ADAPTER

CROSS-REFERENCE TO RELATED APPLICATION

This application is a division of U.S. patent application Ser. No. 16/504,623, filed on Jul. 8, 2019, entitled "Implantable Power Adapter," the disclosure of which is incorporated herein by reference in its entirety.

BACKGROUND

The present disclosure relates generally to the field of implantable devices, and in particular, to a power adapter configured to be used with an implant.

Some known implantable devices receive power and/or energy by transcutaneously applying low frequency electrical current, similar to the transcutaneous energy transfer and application used in some known devices for delivering transcutaneous electrical stimulation. Using low frequencies, however, can cause pain, muscle contraction, discomfort, and other undesirable sensations to a subject when applied to a body of the subject. Sensitivity (e.g., of a body) to a transcutaneous electrical stimulus decreases as the frequency at which the stimulus is applied increases. Thus, a need exists for a power adapter that adapts implantable devices to receive transcutaneous energy at higher frequencies to avoid causing pain, muscle contractions, discomfort, and other undesirable sensations to a body of a subject.

SUMMARY

In some embodiments, an apparatus includes a housing and a circuit at least partially disposed in the housing. The housing can be configured to be coupled to an implantable electrical conductor for disposition in a body. The circuit can be configured to be electrically connected to a pick-up electrode of the implantable electrical conductor when the housing is coupled to the implantable electrical conductor. When the housing is coupled to the implantable electrical conductor and implanted in a body, the circuit is configured to (1) receive, transcutaneously from a power supply, a first energy, (2) convert the first energy to a second energy, and (3) transmit, to the pick-up electrode, the second energy such that the implantable electrical conductor can apply, via a stimulating electrode, the second energy at the second frequency to a region in the body.

BRIEF DESCRIPTION OF THE DRAWINGS

The drawings are not necessarily to scale. The drawings are merely schematic representations, not intended to portray specific parameters of the invention. The drawings are intended to depict only typical embodiments of disclosed systems, apparatus, and methods. In the drawings, like reference characters refer to like elements (e.g., functionally similar and/or structurally similar elements).

FIGS. 5A and 5B are schematic diagrams depicting an effect of using a power adapter in conjunction with a transmitter, in accordance with an embodiment.

FIGS. 5C-5E are waveforms illustrating potential waveforms used with respect to a power adapter, in accordance with an embodiment.

DETAILED DESCRIPTION

In some embodiments, an apparatus includes a housing and a circuit at least partially disposed in the housing (e.g., as part of a power adapter). The housing can be configured to be coupled to an implantable electrical conductor for disposition in a body. The circuit can be configured to be electrically connected to a pick-up electrode of the implantable electrical conductor when the housing is coupled to the implantable electrical conductor. When the housing is coupled to the implantable electrical conductor and implanted in a body, the circuit is configured to (1) receive, transcutaneously from a power supply, a first energy, (2) convert the first energy to a second energy, and (3) transmit, to the pick-up electrode, the second energy such that the implantable electrical conductor can apply, via a stimulating electrode, the second energy at the second frequency to a region in the body.

In some embodiments, an apparatus includes a power adapter having a housing and a circuit at least partially disposed in the housing. The housing can be configured to be coupled to an implantable device for disposition in a body. The circuit can be configured to be electrically connected to the implantable device when the housing is coupled to the implantable electrical conductor. When the housing is coupled to the implantable electrical conductor and implanted in a body, the circuit can be configured to (1) receive, transcutaneously from a power supply, a first energy having a first set of characteristics, (2) convert the first energy to a second energy having a second set of characteristics different from the first set of characteristics, and (3) transfer, to the implantable device, the second energy such that the second energy powers the implantable device.

In some embodiments, a method includes receiving, transcutaneously and from an electrical pulse generator, first energy having a first set of characteristics. The first energy is converted, via a rectification circuit, to a second energy having a second set of characteristics different from the first set of characteristics. The second energy is transferred from the rectification circuit to a stimulating electrode of an implantable electrical conductor such that the implantable electrical conductor applies, via the stimulating electrode, the second energy to a target nerve internal to a body.

Figure 1A:
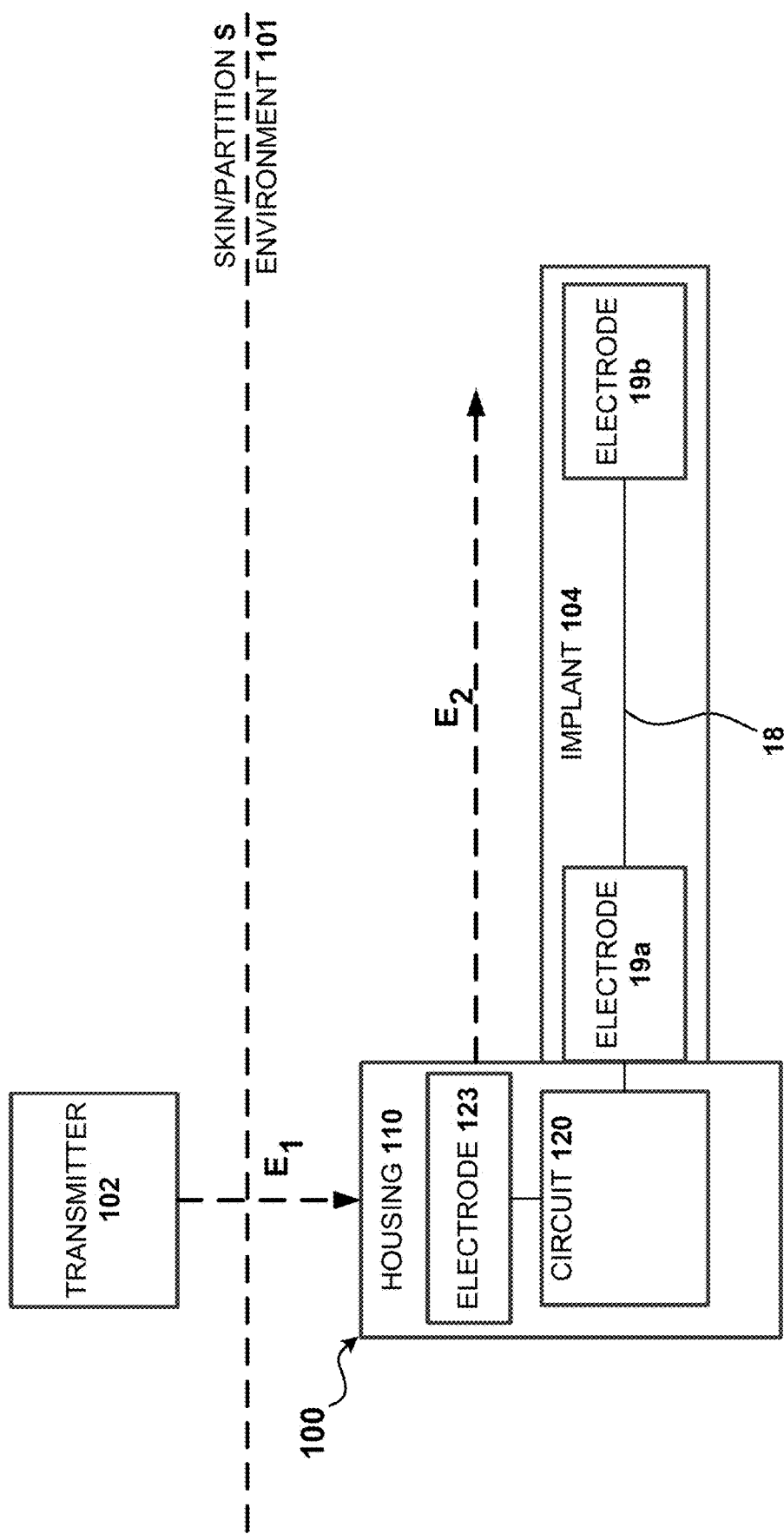
FIG. 1A is a schematic block diagram depicting a power adapter coupled to an implant, in accordance with an embodiment.

FIG. 1A is a schematic block diagram depicting a power adapter 100 coupled to an implant 104, in accordance with an embodiment. As shown in FIG. 1A, the power adapter 100 includes a housing 110, a circuit 120 at least partially disposed in the housing 110 and an electrode 123. The power adapter 100 can be configured to be coupled or interconnected to implant 104 such as at and via the housing 110, as shown in FIG. 1A. The power adapter 100 can be configured to operate, in conjunction with and when coupled to the implant 104, in an environment of and internal to a body, such as environment 101, which can be defined, for example, by a boundary such as skin/partition S, such as shown in FIG. 1A.

Figure 1B:
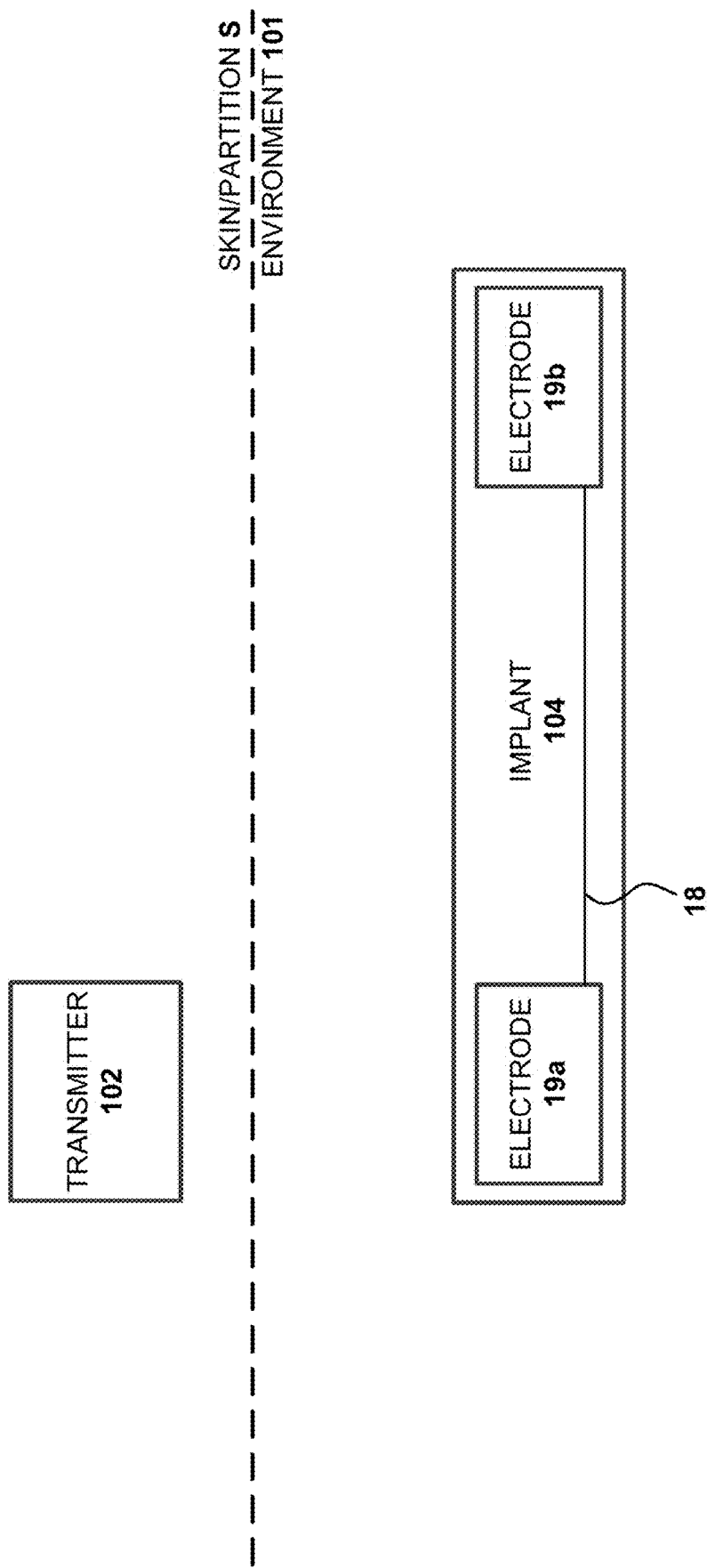
FIG. 1B is a schematic block diagram depicting an implant without a power adapter, in accordance with an embodiment.

FIG. 1B is a schematic block diagram depicting the implant 104 without a power adapter being couple thereto (e.g., the power adapter 100 shown in FIG. 1A). As shown in FIG. 1B, the implant 104 includes electrodes 19a and 19b. The power adapter 100, when coupled to the implant 104 (e.g., at and/or over electrode 19a such as shown in FIG. 1A), can be configured to operate in the environment 101, in conjunction with the implant 104 and a device such as the transmitter 102 to, for example, enable (e.g., supply power to) the implant 104 to perform or otherwise carry out a medical procedure, task, operation, or measurement in the body. More specifically, the electrode 123 can be configured to receive electrical energy from transmitter 102, the circuit 120 can convert the frequency and/or waveform of the electrical energy, and the power adapter 100 can provide the converted electrical energy to the electrode 19a, as described in further detail herein.

For example, the power adapter 100 can be configured to receive, from the transmitter 102 and via the electrode 123, energy $E_1$ (referred to herein as "first energy") such as a first form or quantity of energy, power, or signals (collectively, "energy") having a first characteristic or set of characteristics (e.g., a first frequency, a first waveform, a first burst pattern, and/or the like). The first energy $E_1$, due to the first characteristic(s), may be unsuitable for use in powering and/or to be otherwise provided to or used by the implant 104. Accordingly, to provide energy suitable for use by the implant 104 such that the implant 104 is enabled to perform the medical procedure in the body, the power adapter 100 can be configured to transform, rectify, derive, adapt, and/or otherwise convert the first energy $E_1$ to a second energy $E_2$, including a second form or quantity of energy, power, or signals ("collectively, energy") having a second characteristic or set of characteristics (e.g., a second frequency, a second waveform, a second burst pattern, and/or the like).

As shown in FIG. 1A, the power adapter 100 can be configured to convert the first energy $E_1$ to the second energy $E_2$ such that the second energy $E_2$, due to the second characteristic(s), is suitable for use by the implant 104, such that the implant 104 is enabled to perform, using the second energy $E_2$, the medical procedure in the body (e.g., including providing, via the second energy $E_2$, stimulation, activation, or excitation of tissue, nerves, or muscles in the body). The power adapter 100 can be configured to transfer or input the second energy $E_2$ to the implant 104 to enable (e.g., powering of, or control over) the implant 104 in performing or otherwise carrying out the medical procedure in the body. More particularly, when the power adapter 100 is coupled to the implant 104, the circuit 120 is electrically coupled to the electrode 19a (e.g., via a conductor or the like not shown in FIG. 1A) such that the second energy $E_2$ that is generated by the circuit 120 is provided as an input to the electrode 19a.

The housing 110 can be configured to be coupled to the implant 104 for disposition in a body therewith. The electrode 123 of the power adapter 100 can be configured to receive, transcutaneously with respect to the body, the first energy $E_1$ (e.g., high frequency electrical bursts, low frequency pulses, etc.) for conversion and transfer to implant 104 for application (e.g., in the form of bursts or pulses, to be used by the implant 104, etc.), as described herein. Skin/partition S can include, for example, a barrier, partition, skin, and the like, such as of the body of a subject, including, for example, a person, patient, and the like. The body of the subject can include an (e.g., internal) environment, such as environment 101.

The transmitter 102 can be or include, for example, an external pulse transmitter (EPT), a power source or supply, an energy source or supply, a voltage source or supply, a (wireless) energy transfer device, a signal transmitter, and/or the like. The transmitter 102 can be configured to transmit energy (e.g., the first energy $E_1$) into a body of a subject, which can be received, for example, by the power adapter 100 and used in and/or by implant 104 (e.g., when power adapter 100 is coupled to implant 104). For example, the transmitter 102 can be configured to transmit the energy into the body for receipt, or pick-up (e.g., of some portion of the energy), by the power adapter 100. Subsequently, the energy, after being received by the power adapter 100, can be transferred from the power adapter 100 to the implant 104 (e.g., the second energy $E_2$, shown in FIG. 1A). In some instances, the energy can be converted to a form (e.g., from a first form of energy to a second form of energy) suitable for use in powering the implant 104, such as to enable the implant 104 to perform a medical procedure in the body, as described herein. In other instances, the power adapter 100 can have and/or can be placed in a pass-through configuration and/or state in which the energy received from the transmitter is transferred to the implant without substantially modifying the characteristics of the energy. Accordingly, the second energy $E_2$ transferred from the power adapter 100 to the implant 104 can have characteristics similar to or different from characteristics of the first energy $E_1$ received from the transmitter 102.

The transmitter 102 can be configured to transmit the energy into a body of a subject transcutaneously, at various levels of current, or electrical charge, and at current and/or frequency levels, to avoid causing adverse sensory or motor activation or stimulation (e.g., an undesirable local response) in and by the body. In some instances, the transmitter 102 can deliver energy transcutaneously via hydrogel, wetted cloth, and/or other electrodes attached to the skin. In some instances, the transmitter 102 can be configured to transmit the energy via output of a time-varying voltage (or electrical potential), current (or electrical charge), or electromagnetic field—at a predetermined frequency or range of frequencies, and with a predetermined waveform. In some implementations, the output from the transmitter 102 can include, for example, a time-varying flow of electrical charge. The time-varying flow of electrical charge can include, for example, electrical bursts, electrical pulses, and/or the like ("electrical burst(s)" or "burst(s)"), such as in the form of a train or series of high frequency bursts, including, for example, electrical, electromagnetic, and/or magnetic bursts. In some implementations, the output of the transmitter 102 can include a train or series of low frequency bursts, where each burst includes a single low frequency pulse. In some implementations, the output of the transmitter 102 can include a train or series of bursts including any suitable combination of one or more low frequency energy bursts and one or more high frequency energy bursts. In some instances, the one or more low frequency energy bursts can have one or more characteristics configured to result in a desirable local response in and by the body such as, for example, increased blood flow within a region of the body adjacent to or relatively near the transmitter 102, while the one or more high frequency energy bursts can be received by, for example, the power adapter 100.

Figure 5F:
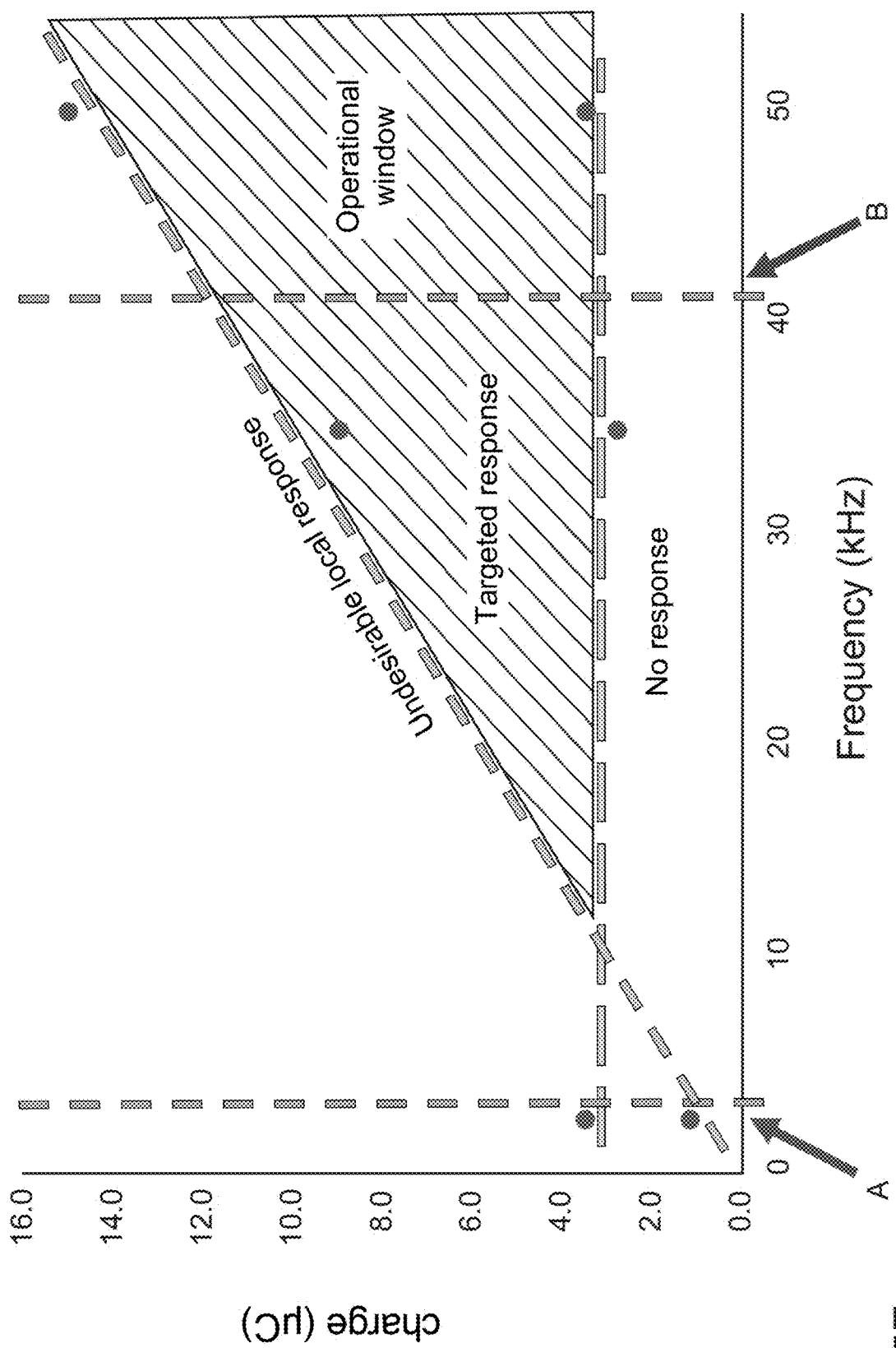
FIG. 5F is a graph illustrating the relationship between charge and frequency when applied to an individual, according to an embodiment.

In some implementations, the predetermined frequency or range of frequencies can include, for example, a frequency or range of frequencies in the range of approximately 10 kilohertz (kHz) to 60 kHz. The predetermined frequency or range of frequencies can otherwise include a frequency or range of frequencies at which the energy output from the transmitter 102 can be applied, such as to a body of a subject, without causing an undesirable response, or stimulation ("response"), such as an undesirable local motor response, in and by the body, such as shown in FIG. 5F. For example, in some implementations, the transmitter 102 can be configured to transmit the energy (e.g., first energy $E_1$) at a frequency and charge configured to avoid causing a sensation or response in or by the body tissues (e.g., a local response). In some implementations, the transmitter 102 can be configured to transmit energy (e.g., the first energy $E_1$) at a frequency and charge configured to cause a desirable local response (e.g., increased blood flow or other desired local responses). In some implementations, the transmitter 102 can be configured to transmit energy (e.g., the first energy $E_1$), in which a first portion of the energy is at a first frequency and/or charge configured to avoid causing a local response and a second portion of the energy is at a second frequency and/or charge configured to cause the desirable local response. In some implementations, the transmitter 102 can be configured to transmit the first portion of the energy and the second portion of the energy in any suitable combination, pattern, interval, sequence, and/or the like.

In some implementations, the predetermined waveform can include, for example, a sinusoidal waveform, a rectangular waveform, a triangular waveform, or any other suitable waveform, such as shown and described with reference to FIGS. 5C-5E. The predetermined waveform can otherwise include any suitable type of waveform. Operating parameters by which the transmitter 102 can be configured to transmit the energy can include, for example, pulse width, pulse frequency, current magnitude, current density, power magnitude, power density, and the like.

The transmitter 102 can be configured to transmit the energy by application of the output to a body of a subject at or with respect to a position, region, or location surrounding, encompassing, or adjacent to a position or location at which the power adapter 100 or the implant 104 are disposed (e.g., implanted) in the body, such as shown in FIG. 1A. For example, the transmitter 102 can be configured to transmit the energy by application of the output to the body, transcutaneously, such as along or with respect to a path (e.g., electrical path, conductive path) at least partially disposed internal to the body, and interconnecting the transmitter 102, the power adapter 100, and the implant 104. That is, the path can be defined, in part, by the body into which the transmitter 102 is configured to transmit the energy, such as by the portion of the body between the transmitter 102, power adapter 100, and implant 104, such as shown and described with reference to FIG. 3.

The implant 104 represents an implant such as an implantable device, including, for example, an implantable electrical conductor, and/or the like ("implant" or "implantable device" or "implantable electrical conductor"). The implant 104 can be configured to be powered by and/or otherwise use energy received from an external device such as an external transmitter or power supply (e.g., transmitter 102), via a power adapter (e.g., power adapter 100), to perform a medical procedure in a body (e.g., in environment 101) of a subject, as described herein. In some implementations, the implant 104 can include an onboard energy source, energy storage device, and/or the like, such as a battery. Such a battery can, for example, store and/or be recharged by the energy received transcutaneously.

For example, in some instances, the implant 104 can be or include an implantable electrical conductor, such as of an implantable stimulation device, or stimulator, configured to operate in the body, and to be powered, via the power adapter 100, by an external device such as the transmitter 102. In these instances, the implantable stimulation device, or stimulator, can be or include, for example, a nerve stimulator, an artificial pacemaker, and/or the like. In other instances, the implant 104 can be or include an implantable electrical conductor, such as of a fluid conveyance device, or fluid conveyor, such as a pump or compressor (e.g., insulin pump), or a vacuum, suction, or depressurizing device. In other instances, the implant 104 can be or include an implantable electrical conductor, such as a sensor, transducer, monitor, and/or recorder, including, for example, an electrocardiography (ECG) sensor, a heart rate monitor, a Holter monitor, and/or the like. The implant can otherwise be or include any suitable type and number of implantable electrical conductors.

As shown in FIG. 1B, the implant 104 includes electrodes 19a and 19b, interconnected over conductor 18. The implant 104 can include an input and an output, such as at the electrode 19a and the electrode 19b, respectively. For example, the implant 104 can be configured to receive energy at the input (e.g., at the electrode 19a), and to provide energy at the output, (e.g., at the electrode 19b). Energy can be conveyed between the input (e.g., electrode 19a) and the output (e.g., electrode 19b) via an implantable electrical conductor (e.g., conductor 18) of the implant 104. The implant 104 can be configured to receive, transcutaneously and at the electrode 19a, energy from a transmitter such as transmitter 102. The energy can be received, for example, to power the implant 104, to control the implant 104 (e.g., as in performing a medical procedure), and/or the like.

In some implementations, the implant 104 can be configured to receive energy from the transmitter 102 via the power adapter 100. For example, in some instances, such as when the power adapter 100 is connected to the implant 104, as shown in FIG. 1A, the power adapter 100 can be configured to receive the first energy $E_1$ (e.g., having a first frequency, waveform and/or other characteristic) from the transmitter, for conversion of the first energy to the second energy $E_2$ (e.g., having a second frequency, waveform and/or other characteristic), and transfer of the second energy $E_2$, from the power adapter 100 and to the implant 104, such as by input to the implant 104 at the electrode 19a, such that the implant 104 receives the second energy $E_2$ (e.g., for output at electrode 19b). In some implementations, when the power adapter 100 is not connected to the implant 104 (e.g., as shown in FIG. 1B), the electrode 19a can receive the second energy $E_2$ directly. By connecting the power adapter 100 to the implant 104 and over the electrode 19a, the implant 104 can be retrofitted and/or adapted to receive the first energy $E_1$ rather than the second energy $E_2$. That is, when the power adapter 100 is connected to the implant 104, such as shown in FIG. 1A, the power adapter 100 can prevent the electrode 19a from directly receiving energy. The energy output by electrode 19b can be detected and/or received by the transmitter 102 (e.g., by a skin electrode (not shown in FIG. 1A or 1B) to complete an electrical circuit including the transmitter 120, the housing 110 and the implant 104.

The electrodes 19a and 19b can each include one or more electrodes, electrical contacts, electrical terminals, and the like. The electrode 19a can include an input electrode and the electrode 19b can include an output electrode. For example, the electrode 19a can include an input electrode such as a receiving electrode, a pick-up electrode, and/or the like (referred to herein as "pick-up electrode"). In some implementations, such as those in which the implant 104 is a stimulation device, the electrode 19b can include an output electrode such as a stimulating or stimulation electrode, a stimulation lead, and/or the like (referred to herein as "stimulating electrode" or "stimulation electrode"). In some implementations, the electrode 19a can include or be formed of a material such as a material composed of titanium (Ti), titanium-nitride (TiN), platinum-iridium (Pt—Ir) compound, and/or the like. In some implementations, the electrode 19b can include or be formed of a material such as a material composed of platinum (Pt), iridium (Ir), a platinum-iridium (Pt—Ir) compound, or alloy, and/or the like. The conductor 18 can include any suitable electrical conductor, electrical lead, and/or conductive material over which the electrodes 19a and 19b can be interconnected. For example, the conductor 18 can include a path such as a conductive path or an electrical path configured to interconnect the electrodes 19a and 19b over the implant 104. The conductor 18 can include or be formed of a material such as an inert or non-reactive material, or any other material suitable for use in a body of a subject, in accordance with embodiments described herein.

The housing 110 can be or can include any suitable type of housing or casing. For example, the housing 110 can include a housing such as an hermetically sealed casing, or can, configured to house or otherwise contain one or more circuits (e.g., circuit 120), and, having a feedthrough, inner contact (e.g., electric conductor), one or more mating features (e.g., grip mechanism assembly) configured to electrically and mechanically couple to and make contact with a pick-up electrode (e.g., electrode 19a of implant 104), and a sleeve (e.g., for mechanical and/or electrical protection). The housing 110 can be configured to at least partially house one or more circuits, including, for example, the circuit 120. The housing 110 can be configured to be coupled to an implant such as implant 104 for disposition, with implant 104 (and the circuit 120), in a body of a subject. The housing 110 can be configured to mechanically insulate the circuit 120 from the body, including, for example, from an environment in the body such as environment 101. For example, the housing 110 can be configured to insulate the circuit 120 from, for example, an environment such as environment 101 in the body of the subject, such as when the housing 110 is coupled to implant 104 and disposed in environment 101, such as by implantation with implant 104 in the body. The housing 110 can include any suitable housing capable of attaching, coupling, connecting, interconnecting, or otherwise being added, mechanically, electrically, and otherwise, to an implant such as implant 104, as described herein. The housing 110 can include any suitable type and number of components, such as including resistors, capacitors, transistors, diodes, inductors, an energy source, energy storage device, and/or the like. In some implementations, the housing 110 does not include an energy source, energy storage device, and/or the like, which can be or include, for example, a battery or other chemical source of energy. In other implementations, the housing can include an energy storage device (e.g., battery, energy storage capacitor, etc.) that can be used to power the implant 104 and/or can be recharged by receiving the transcutaneous transfer of energy, as described herein. In some implementations, the housing 110 can be or include, for example, a hermetically sealed can configured to at least partially house the circuit 120.

The circuit 120 can be or include a circuit such as an integrated circuit (IC), and/or the like. The circuit 120 can be configured to be electrically connected to an implantable device such as the implant 104 when the housing 110 is coupled to the implant 104, such as at the electrode 19a. For example, the circuit 120 can be configured to electrically connect to the implant 104, when the housing 110 is coupled to the implant 104, such as at a pick-up electrode (e.g., electrode 19a) of the implant 104, to enable the circuit 120 to provide energy (e.g., transformed power, conditioned signals) to the implant 104. The energy can be provided, by the circuit 120 and to the implant 104, via input to the implant 104 at the pick-up electrode (e.g., via a conductor or electric interface in electric communication with the electrode 19a). The circuit 120 can be configured to receive the energy (e.g., for conversion of the energy and transfer of the converted energy to implant 104) from a transmitter such as transmitter 102, as described herein. The circuit 120 can include various components, such as described herein with reference to FIG. 2.

As an example, in use, the power adapter 100 can be configured to be implanted, in a coupled or interconnected state with implant 104, in a body of a subject. For example, the power adapter 100 can be configured to be coupled to implant 104 by attachment of the housing 110 over a pick-up electrode (electrode 19a) of the implant 104. In some instances, the power adapter 100 can be configured to be retrofit to an existing implant in a body of a subject, such as the implant 104. For example, the power adapter 100 can be configured to be mated to the existing implant such as by crimping, or the like. Once the power adapter 100 is implanted in the body with the implant 104, operating parameters, including, for example, stimulation parameters, and the like, can be set (e.g., at transmitter 102), as described herein. Accordingly, the power adapter 100—along with the transmitter 102 and the implant 104—can be configured for use, such as by the subject of the body (in which the power adapter 100 is implanted with the implant 104).

In other implementations, the power adapter 100 can be integral to the implant 104. For example, in some implementations, the power adapter 100 can be provided as part of or embedded in the implant 104, such as in a pre-coupled or -interconnected state with the implant (e.g., via interconnection to electrode 19a). Similarly stated, in such implementations, the functions of the power adapter 100 (as described herein) can be part of and/or integrated into the implant. In such implementations, a separate power adapter 100 is not needed and/or used to receive the transcutaneous energy transfer.

In some implementations, such as those in which the implant 104 is a stimulation device and the electrode 19b includes an output electrode such as a stimulating electrode, the power adapter 100 can be configured to convert the first energy $E_1$ (e.g., from transmitter 102) to the second energy $E_2$, for input of the second energy $E_2$ to the implant 104 to enable the implant 104 in performing a medical procedure. In such implementations, the medical procedure can include, for example, a medical procedure in which the implant 104 is configured to provide stimulation, activation, excitation, and the like ("stimulation") of tissue, nerves, or muscles in a body of a subject. In such implementations, the implant 104 can be configured to perform the medical procedure in the body via output of the second energy $E_2$ at the electrode 19b. In such implementations, the second energy $E_2$ can include, for example, a sequence of low frequency pulses or bursts and/or a sequence of high frequency pulses or bursts. Specifically, the second energy $E_2$ can include, for example, interlaced delivery of low and high frequency energy, stimulation, bursts, and/or pulses. The medical procedure can be performed, for example, to activate a cutaneous receptor, a muscle, and/or a nerve of the body.

Figure 2:
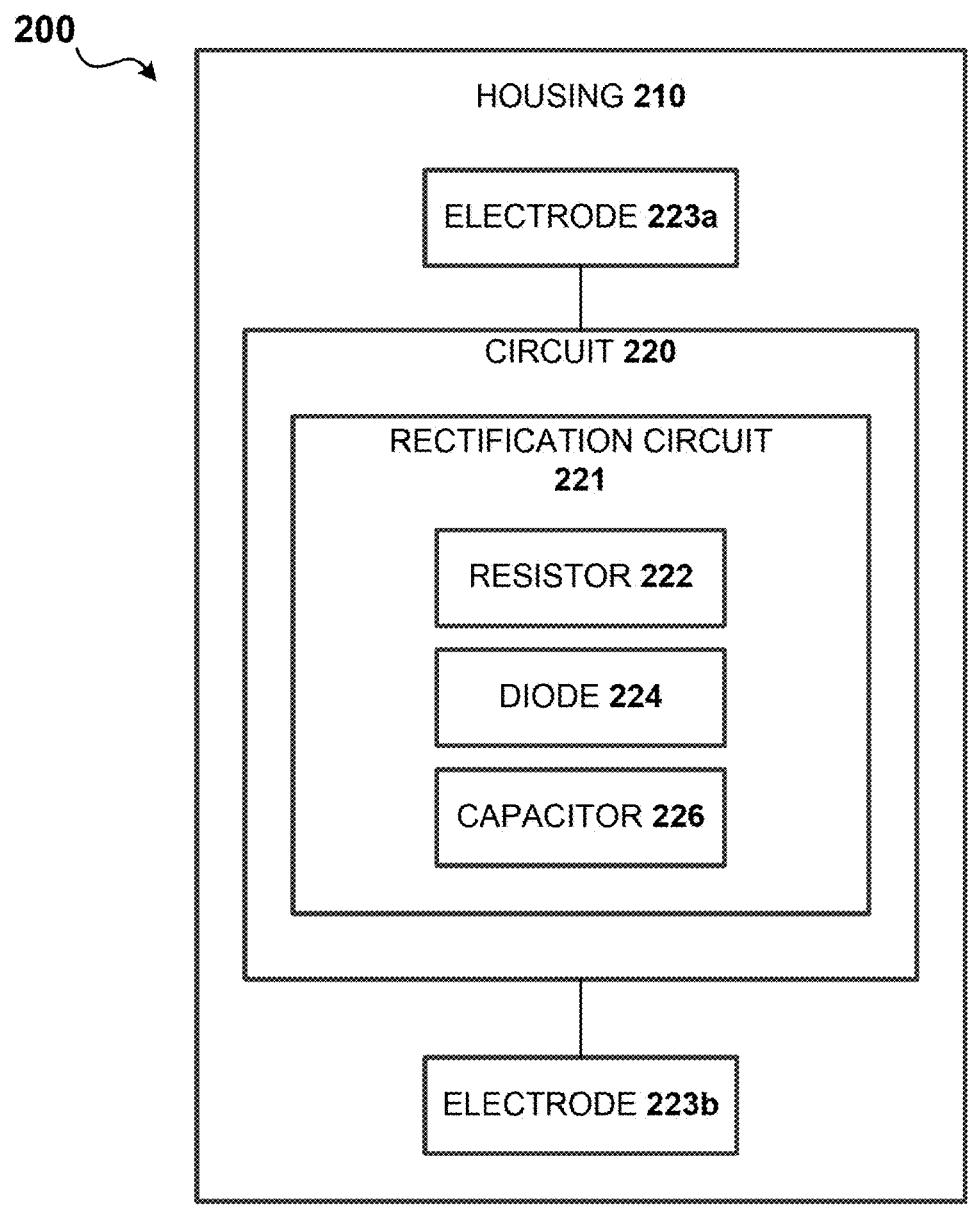
FIG. 2 is a schematic block diagram depicting a power adapter, in accordance with an embodiment.

FIG. 2 is a schematic block diagram depicting a power adapter 200, in accordance with an embodiment. As shown, the power adapter 200 includes a housing 210 and a circuit 220 at least partially disposed in the housing 210. The power adapter 200 can be configured to be coupled or interconnected to an implant (e.g., the implant 104) for disposition in a body, such as to operate in an environment (e.g., the environment 101) of and internal to the body. The circuit 220, when the housing 210 is coupled to an implant (e.g., the implant 104) and implanted in a body, can be configured to electrically interconnect (e.g., via an electrode 223b) to a stimulating electrode of the implant. The power adapter 200 can be structurally and/or functionally similar to other power adapters (e.g., the power adapter 100) shown and described herein.

The circuit 220 includes a rectification circuit 221 and an electrode 223a (e.g., pick-up electrode). The rectification circuit 221 can be or include, for example, a halfwave-rectification circuit or a fullwave-rectification circuit. For example, in some instances, the rectification circuit 221 can include a resistor 222, a diode 224, and a capacitor 226. While not shown or described with respect to FIG. 2, in other implementations (e.g., as shown and described with respect to 9A, 9B and/or 10), the circuit can include another capacitor and/or an inductor to provide protection at frequencies used with respect to Mill devices. The rectification circuit 221 can be configured to selectively convert received energy (e.g., received from the transmitter 102 via the electrode 223a). For example, the rectification circuit 221 can be configured to convert first energy by rectification of the first energy to provide second energy (e.g., via the electrode 223b). In some instances, the second energy can be substantially positive DC or substantially negative DC. As an example, the rectification circuit 221 can be configured to convert and filter received signals in a manner similar to that of an amplitude modulation (AM) receiver.

The capacitor 226 can be or include, for example, a direct current (DC) blocking capacitor. The capacitor 226 can be configured to maintain a level of charge balance of the rectification circuit 221. For example, the capacitor 226 can be configured to provide charge balancing of energy transmitted from the rectification circuit 221. In some implementations, such as those in which the implant 104 is a stimulation device, a type or characteristic of the capacitor 226 can be chosen, for example, based on a characteristic (e.g., operating condition) such as tissue-electrode capacitance, such as of a pick-up electrode (e.g., electrode 19a) and a stimulating electrode (e.g., electrode 19b) of the implant 104, with respect to tissue internal to a body of a subject (e.g., in environment 101). In such implementations, the capacitor 226 can effectively be connected in series with the pick-up electrode and the stimulating electrode. In a serial connection of capacitors, the capacitor with the least amount of capacitance (i.e., the capacitor with the smallest measure of capacitance) determines the combined capacitance of the capacitors (e.g., which is substantially equal to the capacitance of the capacitor with the least relative amount of capacitance). Accordingly, the capacitor 226 can be chosen or configured to have a particular value or measure of capacitance to not decrease the overall capacitance of the path (e.g., interconnecting the capacitor 226, the pick-up electrode, and the stimulating electrode) based on the effective capacitance of the tissue-electrode capacitance of the pick-up electrode and the stimulating electrode.

As an example, where the tissue-electrode capacitance is approximately 4 microfarad (µF), the capacitor 226 can be chosen or configured to have a value or measure of capacitance of approximately 4 µF, or greater. In this example, the value of the capacitor 226 can be chosen or configured based on the tissue-electrode capacitance of the tissue internal to the body and the pick-up electrode (e.g., electrode 19a) and the stimulating electrode (e.g., electrode 19b) of the implant 104. In some implementations, the capacitor 226 can be chosen or configured to have a value or measure of capacitance that does not decrease, but supports and/or maintains an overall capacitance of the conductive path (e.g., the path interconnecting a pick-up electrode with a stimulating electrode) of the implant 104.

The diode 224 can be or include, for example, a rectifying diode. In some implementations, the diode 224 can be or include a rectifying diode such as a Schottky diode, a silicone diode, and/or the like. In some implementations, a type or characteristic of the diode 224 can be chosen, for example, based on a characteristic such as a magnitude of a voltage drop (e.g., in a forward direction) over the diode 224. For example, the type of the diode 224 can be chosen to reduce a magnitude of the voltage drop over the diode 224. In this example, the type of the diode 224 can be chosen to be or include a Schottky diode (e.g., instead of a silicon diode) to reduce the magnitude of the voltage drop over the diode 224 (e.g., compared to that of the silicon diode), and to thereby achieve a higher pick-up ratio (e.g., compared to that of a silicone diode). In some implementations, a type of the diode 224 can be chosen based on or to facilitate any suitable characteristic, such as amount of leak current, amount of back leak current, a discharge rate (e.g., of capacitor 226) between applied electrical bursts, and/or the like. For purposes of the present disclosure "pick-up" ratio refers to the amount of energy received by the implant relative to the amount of energy sent by the external transmitter. For example, a pick-up ratio of 0.5 indicates that the amount of energy received is approximately half the amount of energy sent.

The resistor 222 provides a discharge path (from rectification circuit 221) for the capacitor 226. In some implementations, a type or characteristic of the resistor 222 can be chosen, for example, based on a characteristic of the rectification circuit 221 including, for example, a discharge path characteristic of the rectification circuit 221. For example, the resistor 222 can be chosen to have a measure or value of resistance greater than an effective resistance of the diode 224, to prevent bypass (e.g., by electrical current) of the diode 224 in use (e.g., of the power adapter 200 with an implant such as implant 104). In some implementations, a type or characteristic of the resistor 222 can be chosen, for example, based on an applied frequency or frequency range of the energy (e.g., electrical signals, electrical bursts) from transmitter 102, a burst repetition frequency of the applied frequency or frequency range of the energy, a burst duration of the applied frequency or frequency range of the energy, and/or the like.

Figure 3:
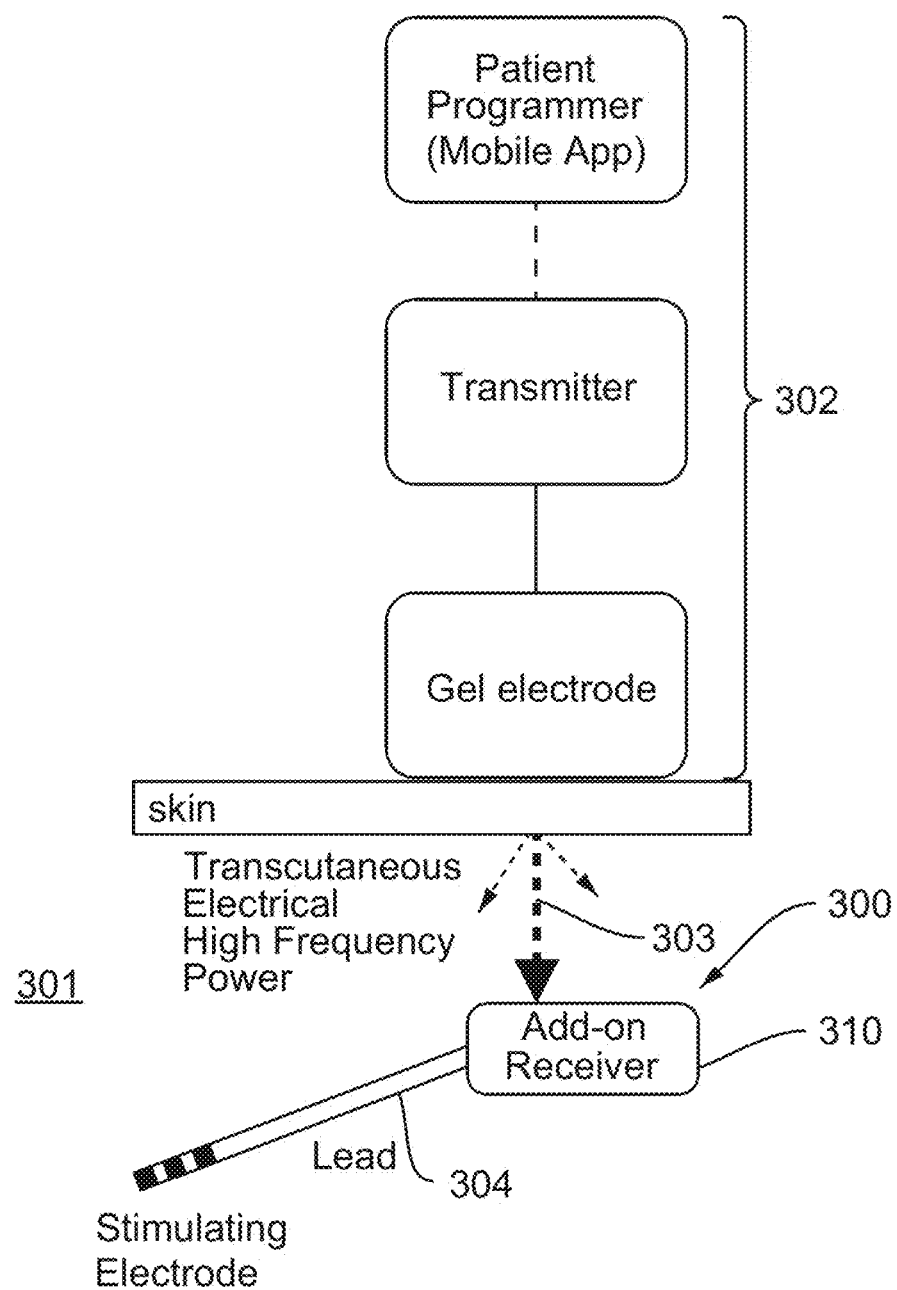
FIG. 3 is a schematic block diagram depicting an example of use of an apparatus in conjunction with a transmitter, in accordance with an embodiment.

FIG. 3 is a schematic block diagram depicting an example use of a power adapter 300 in conjunction with a transmitter 302, in accordance with an embodiment. As shown, the power adapter 300 includes a housing 310 (labeled "add-on receiver") and a circuit (not shown) at least partially disposed in the housing 310. The power adapter 300 can be structurally and/or functionally similar to other power adapters (e.g., 100, 200) described herein.

The transmitter 302 can be configured to send or otherwise provide energy to power adapter 300 (for powering and/or supplying energy to implant 304) via path 303. In some implementations, the electrical pulse generator (e.g., transmitter 102, transmitter 302) can include, for example, a power supply. The path 303, along which the energy is received, transferred, and applied, can include, for example, a portion of the body of the subject between the transmitter 302 (e.g., at a gel and/or cloth electrode of the transmitter (not shown)) and the power adapter 300 (when disposed with implant 104 in the body).

For example, the power adapter 300, the housing 310, and the circuit can be structurally and/or functionally similar to the power adapter 100, the housing 110, and the circuit 120, respectively, as described herein. The power adapter 300 can be configured to be coupled, via the housing 310, to an implant such as implant 304 for disposition in a body with implant 304, such as beneath skin and in environment 301 of the body. The power adapter 300 can be configured to be attached or coupled to implant 304 such that the pick-up electrode of implant 304 is electrically insulated from the environment 301 (e.g., when implant 304 and power adapter 300 are implanted in a body). The power adapter 300 can be configured to receive energy from the transmitter 302 for conversion and transfer to implant 304, and application, via a stimulating electrode of implant 304, to a target site or object in the body.

The transmitter 302 can be structurally and/or functionally similar to the transmitter 102, as described herein. For example, the transmitter 302 can include an external transmitter (labeled "transmitter") and a patch (not shown) including one or more gel electrodes (labeled "gel electrode"). In some implementations, the external transmitter can include, for example, a high frequency transmitter. While shown in FIG. 3 as gel electrodes, in some implementations, the patch can include, for example, a gel patch, a hydrogel patch, a cloth patch, and/or the like, including, for example, electrodes such as gel electrodes, hydrogel electrodes, cloth electrodes, and/or the like. In some implementations, the patch can include a disposable patch. The transmitter 302 can be configured to transmit energy transcutaneously into the body of a subject (e.g., for receipt by the circuit disposed in the housing 310), such as by application, via the patch, of the output of the transmitter 302 to the body.

Implant 304 can be structurally and/or functionally similar to implant 104, as described herein. For example, implant 304 can include an electrical conductor or lead (labeled "lead"), a stimulating electrode (labeled "stimulating electrode"), and a pick-up electrode (not shown), over which the power adapter 300 can be attached or coupled, such as described herein with reference to FIG. 1, and shown in FIG. 3. The lead of implant 304 can include, for example, a conductive path interconnecting the stimulating electrode and the pick-up electrode. The lead of implant 304 can be or include, for example, an electrical conductor such as a coiled wire (Pt—Ir) conductor disposed within a silicone sheath, or tubing. For example, the lead of implant 304 can be insulated (e.g., from tissue in the environment 301) by the silicone tubing and by silicone backfill disposed in and configured to close the tubing at each end. Implant 304 can be configured to receive, transcutaneously and via the power adapter 300 (e.g., disposed at the pick-up electrode of implant 304), energy (e.g., electrical signal, electromagnetic signal, magnetic signal) from the transmitter of the transmitter 302. For example, implant 304 can be configured to receive the energy to apply, via the stimulating electrode, a stimulus (e.g., electrical bursts, electrical pulses) to a target site or object in a body of a subject. In some implementations, implant 304 can include, for example, three or more stimulating electrodes (e.g., such as the electrode 19*b*).

In use, the power adapter 300 can be configured to receive, transcutaneously from the transmitter 302, transdermal high frequency bursts of energy (e.g., electrical energy). The energy can be received at, or can otherwise include, for example, a first frequency of between about 30 kHz and 100 kHz, or greater. In other instances, the first frequency can be between 100 kHz and 3 megahertz (MHz). In yet other instances, the first frequency can be 10 MHz or less and/or any other suitable frequency. The received energy can be converted, by the power adapter 300, to a form suitable for use in providing stimulation, activation, or excitation (e.g., of tissue, nerve, muscle) in a body of a subject. For example, the received energy can be converted, by the power adapter 300, to a second energy (e.g., stimulation current) having a second frequency less than the first frequency, such as, for example about 1 kHz. In other implementations, the second frequency can be between 1 kHz and 10 kHz. In yet other implementations, the second frequency can be between 500 Hz and 30 kHz. The energy conversion can include, for example, rectification and charge balancing via the power adapter 300. The converted energy can be transferred, from the power adapter 300 to a stimulating electrode of the implant 304, for application to a target in the body (e.g., nerve) at the stimulating electrode.

As an example, the implant 304 can be or include a lead such as a flexible electrical conductor having a length of approximately 15 cm and a diameter of approximately 1.2 mm. The stimulating electrode of the implant 304 can be positioned at or near a target object in the body, such as a nerve, or the like. The pick-up electrode of the implant 304 can be covered by attachment of the power adapter 300 to the end of the implant 304 at which the pick-up electrode is disposed. The target object can include any suitable point, region, or part of interest, such as a nerve (e.g., peroneal nerve, peripheral nerve, etc.). In some implementations, the implant 304 can include, for example, one or more stimulating electrodes having dimensions in the range of approximately 1 mm in length. In some implementations, where the implant 304 includes three or more stimulating electrodes, the stimulating electrodes can be spaced along the lead of the implant 304 at a spacing of approximately 1 mm apart. In some implementations, one or more of the stimulating electrodes of the implant 304 can be manufactured or assembled by coiling of an electrical conductor (e.g., the lead of the implant 304) on the outside of the silicone tubing (e.g., silicone sheath) and at the end of the lead, such as shown in FIG. 3. A conductive surface of the stimulating electrode (e.g., at the stimulation end of the implant 304) can be configured to be in contact with surrounding tissue in the environment 301 when implanted (e.g., with the power adapter 300) in the body. In some implementations, the implant 304 can include, for example, an anchor (e.g., hook, tines) having a diameter of approximately 1.5 mm. The anchor can be configured to fix the implant 304 in position, or otherwise prevent lead migration in the environment 301 upon implantation and positioning of the implant 304 with the power adapter 300 in a body of a subject. For example, the anchor can include a silicone anchor having four prongs or hooks, and can be disposed at the stimulation end of the implant 104.

In some implementations, the transmitter 302 can optionally be configured to be used or programmed for use via software (e.g., residing on a device external to the transmitter). For example, the software can reside or otherwise be hosted on any suitable type of compute device (e.g., mobile device, tablet computer, server). For example, the software can be executed at a compute device to generate and send signals (e.g., including commands) to the transmitter 302 for execution (e.g., at the transmitter 302), and the transmitter 302 can be configured to receive, from the compute device, one or more of the signals, including, for example, a signal corresponding to a command configured to be executed at the transmitter 302. The signals can include, for example, machine- or processor-readable code and/or instructions configured to be stored on and/or executed at the transmitter 302. In some implementations, the code can include instructions configured to be executed at the transmitter 302, such as to set or specify one or more operating parameters, stimulation parameters, and/or the like, of and/or at the transmitter 302. For example, one or more of the operating parameters of the transmitter 302 can include a particular stimulation routine to be applied (e.g., via the implant 104), a particular stimulation intensity to be applied (e.g., transcutaneously to the body), an applied frequency or frequency range of the energy to be applied, and so on. The software can be configured for use, for example, by a user or operator such as a clinician, a patient, and/or the like.

In some implementations, the software by which the transmitter 302 can optionally be configured to be used or programmed for use can be stored, for example, at a compute device such as a tablet compute device. In some instances, the compute device can be configured to communicate with the transmitter 302 via a communications link such as a Bluetooth Low Energy (BLE) communications link, or the like. In some instances, the software can be configured to enable access to data including, for example, patient demographic information, session data, patient stimulation profiles, and the like. In some instances, the software can reside or otherwise be hosted for use via a smartphone platform (e.g., iOS, Android). In some instances, the software can include, for example, a mobile app. In some implementations, the software can be configured to enable, for example, use tracking, system error or fault notification, and/or the like. In some implementations, the software can be configured to control various functions of the transmitter 302, including, for example, selection of a stimulation program or routine (e.g., as pre-defined by a user such as a clinician), stimulation activation and deactivation (e.g., turning the transmitter 302 on and off), increase or decrease (applied) stimulation intensity, and so on. In some implementations, the software can be configured to provide (e.g., via a display, transducer such as a speaker) an indication (e.g., visual, auditory) as to operating status, such as with respect to selected stimulation program, selected stimulation intensity level, good or bad electrode connection, among other types of indications of errors or operating status.

Figure 4:
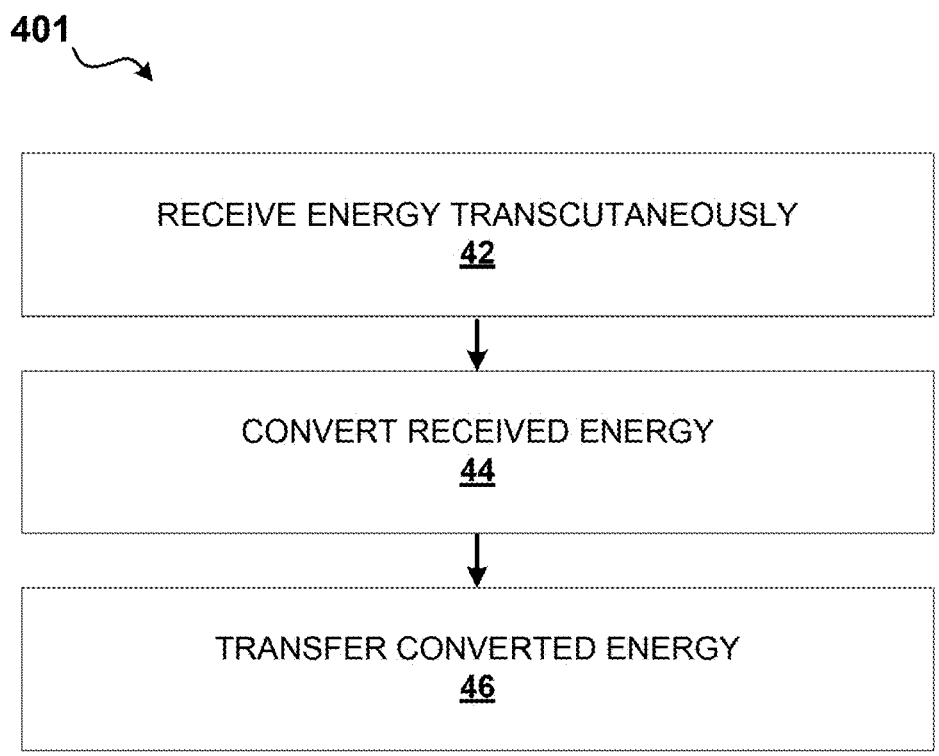
FIG. 4 is a flowchart depicting a method of using a power adapter, in accordance with an embodiment.

FIG. 4 is a flowchart depicting a method 401 of using a power adapter, in accordance with an embodiment. The power adapter can be structurally and/or functionally similar to any of the power adapters (e.g., 100, 200, and/or 300) described herein.

At 42, the method 401 includes receiving (e.g., via the power adapter 100, 200, and/or 300), transcutaneously and from an electrical pulse generator (e.g., the transmitter 102 and/or 302), first energy at a first frequency and/or first waveform. At 44, the method 401 includes converting, via a rectification circuit (e.g., the rectification circuit 221), the first energy to a second energy. In some implementations, the second energy can have a second frequency different from the first frequency and/or a second waveform different from the first waveform. At 46, the method 401 includes transferring, from the rectification circuit, the second energy to a stimulating electrode (e.g., the electrode 19b shown in FIGS. 1A and 1B) of an implantable electrical conductor (e.g., the implant 104 and/or 304) such that the implantable electrical conductor applies, at the second frequency and via the stimulating electrode, the second energy to a target internal to a body (e.g., of a subject). The target internal to the body can include, for example, a nerve, a region in the body, and/or the like.

In some implementations, the second energy can be transferred from the rectification circuit (e.g., the rectification circuit 221) to a pick-up electrode (e.g., the electrode 19a) of the implantable electrical conductor (e.g., the implant 104), for subsequent transfer and routing via the implantable electrical conductor (e.g., the conductor 18 of the implant 104) to the stimulating electrode (e.g., the electrode 19b), and application, at the stimulating electrode, to a target nerve internal to the body. In some implementations, the second energy can be transferred from the rectification circuit to the implantable electrical conductor, and in particular, the stimulating electrode, to enable application of the second energy to the target internal to the body. In some implementations, the first energy can include, for example, alternating current. In some implementations, the second energy can include, for example, pulsating direct current. In some implementations, the first frequency can include, for example, a frequency in the range of about 30 kHz and 100 kHz. When the apparatus is not coupled to the implantable electrical conductor (e.g., via the housing 110, 210, and/or 310), the pick-up electrode of the implantable electrical conductor can be configured to receive, transcutaneously (e.g., from the electrical pulse generator), third energy at substantially the second frequency and/or second waveform.

FIGS. 5A and 5B are schematic diagrams depicting an effect of using a power adapter 500 in conjunction with a transmitter (e.g., the transmitter 502b) and the implant 504, in accordance with an embodiment. The power adapter 500 can be structurally and/or functionally similar to other power adapters (e.g., the power adapter 100, 200, and/or 300) described herein. The implant 504 can be structurally and/or functionally similar to the implants or implantable electrical conductors (e.g., the implant 104 and/or 304) described herein.

With reference to FIG. 5A, transmitter 502a (labeled "External Transmitter (low frequency)") can be configured to apply transcutaneous stimulation (e.g., first energy) via an electrode patch 57a (e.g., disposed at a skin surface) into a body of a subject. The transmitter 502a can be or include, for example, a low frequency external transmitter, and/or the like, configured to operate in conjunction with the implant 504 (e.g., without the power adapter 500). The transmitter 502a can be structurally and/or functionally similar to any of the transmitters (e.g., the transmitter 102), as described herein.

The transmitter 502a can be configured to transmit the energy by application (e.g., via the electrode patch 57a) of the output to the body (e.g., at a skin surface of the body), transcutaneously, such as along or with respect to a path (e.g., electrical path, conductive path) at least partially disposed internal to the body, and interconnecting the transmitter 502a and the implant 504. The path can include, for example, the electrode patch 57a, a first portion of the body 50a, the implant 504 (e.g., via the electrodes 59a and 59b), a second portion of the body 50b, an electrode patch 57b, and the transmitter 502a. A portion of the applied transcutaneous stimulation (e.g., 10%-20%) can be picked up or received by the implant 504, at electrode 59a, and can be transferred and/or routed, to electrode 59b and along the implant 104 (e.g., via the conductor 18). The electrode 59a can include, for example, a pick-up electrode. The electrode 59b can include, for example, a stimulating electrode.

In some implementations, the implant 504 can include insulation such as a silicone backfill and tubing, disposed about a lead body (e.g., the conductor 18 shown in FIGS. 1A and 1B) of the implant 504, such that energy (e.g., electrical pulses received via the electrode 59a) can be transmitted efficiently to the conductive surfaces of the stimulation electrode contacts (e.g., of the electrode 59b), where the electrical current can then be applied to a target such as a target peripheral nerve, or any other suitable site in the body, as described herein. In some implementations, the lead body (e.g., the conductor 18 shown in FIGS. 1A and 1B) of the implant 504 can include, for example, a Pt—Ir lead.

In some implementations, the energy frequency 51a at the pick-up electrode and the energy frequency 51b at the stimulating electrode can be similar, or substantially equal or identical. In some implementations, the waveform can also be similar, or substantially equal or identical, with the exception of the signal amplitude. The transmitter 502a can be configured to apply and deliver energy transcutaneously at a low applied frequency or frequency range (e.g., below 10 kHz) for stimulation at the low applied frequency at and by the electrode 59b.

With reference to FIG. 5B, transmitter 502b (labeled "External Transmitter (high frequency bursts)") can be configured to send or transmit first energy (e.g., energy including high frequency bursts) via electrode patch 57a (e.g., disposed at a skin surface) into a body of a subject, such as described herein. The transmitter 502b can be or include, for example, a high frequency external transmitter, and/or the like, configured to operate in conjunction with the implant 504 via power adapter 500. The transmitter 502b can be structurally and/or functionally similar to transmitters (e.g., the transmitter 102 and/or 302) described herein.

The transmitter 502b can be configured to send the first energy at a frequency of approximately 35 kHz-50 kHz, to avoid causing sensation in the body of the subject. The transmitter 502b can be configured to send the first energy at a frequency to avoid causing direct activation of the nerves about the location of application of the transcutaneous stimulation to the body. The transmitter 502b can be configured to transmit the energy by application (e.g., via the electrode patch 57a) to the body (e.g., at a skin surface of the body), transcutaneously, such as along or with respect to a path (e.g., electrical path, conductive path) at least partially disposed internal to the body, and interconnecting the transmitter 502b, the power adapter 500, and the implant 504. The path can include, for example, the electrode patch 57a, a first portion of the body 50a, the power adapter 500 (e.g., via the electrode 123 and/or 223a in FIGS. 1 and 2, respectively), the implant 504 (e.g., via the electrodes 59a and 59b), a second portion of the body 50b, an electrode patch 57b, and the transmitter 502b.

A portion of the applied transcutaneous stimulation such as between approximately 10%-20% (e.g., from the transmitter 502b) can be picked up by the pick-up electrode of the power adapter 500, in the form of the first energy 52a (e.g., having a first frequency and/or having a first waveform) and converted, by a rectification circuit (e.g., the rectification circuit 221) of a circuit (e.g., the circuit 120 and/or 220) of the power adapter 500 (e.g., at least partially disposed in the housing 510 of the power adapter 500), to second energy 52b (e.g., having a second frequency and/or having a second waveform). The second energy 52b can include, for example, low frequency bursts, high frequency bursts, and/or the like. The second energy 52b can be routed to the electrode 59b for application, via one or more electrodes at or of the electrode 59b, to a target such as a target peripheral nerve, or any other suitable site in the body, such as to treat pain. In some implementations, the second energy 52b can include, for example, a sinusoidal waveform, a rectangular waveform, a triangular waveform, or the like. For example, the power adapter 500 (via the circuit disposed in the housing 510) can be configured to operate in a manner similar to that of an AM radio receiver, by demodulating energy including signals such as high frequency bursts (e.g., carrier wave) and detecting the low frequency (e.g., modulated) signal. As such, the power adapter 500 can be configured to be retrofit and/or adapted for use in or with an implant (e.g., the implant 504) normally configured to receive energy at a first frequency (e.g., a low frequency) and/or having a first waveform, such that the implant can receive energy at a second frequency (e.g., low frequency pulses, high frequency bursts) and/or having a second waveform.

In some implementations, the rectification circuit of the circuit at least partially disposed in housing 510 of the power adapter 500 can include a rectifying diode (e.g., the diode 224) oriented in a cathodic orientation, such as shown in FIG. 5B, such that cathodic stimulation is provided via the stimulating electrode (of the implant 504). In some implementations, the rectification circuit of the circuit at least partially disposed in housing 510 of the power adapter 500 can include a rectifying diode (e.g., the diode 224) oriented in a cathodic orientation such that cathodic stimulation is provided via the stimulating electrode (of the implant 504). The nerve (e.g., sensory, motor) activation threshold in the cathodic orientation (e.g., negative pulse delivered to the stimulating electrode) is lower than that of an anodic orientation of the rectifying diode (e.g., the diode 224) as it causes more effective depolarization of the cell membrane and subsequent activation of the nerve. In some implementations, the housing 510 can be or include a hermetically sealed housing made of Titanium. The first energy (e.g., current at first frequency) applied by the transmitter 502b can be returned, transcutaneously and from the stimulating electrode, to the transmitter in the form of the second energy (e.g., current at second frequency) to complete the electrical circuit. For example, the rectifying diode (e.g., the diode 224) can be oriented to be connected to the stimulating electrode of the implant 504. In other implementations, the rectifying diode (e.g., the diode 224) can be oriented in an anodic orientation such that anodic stimulation is provided via the stimulating electrode (of the implant 504).

FIGS. 5C-5E are waveforms illustrating potential waveforms used with respect to a power adapter, in accordance with an embodiment. As shown in FIG. 5C, waveform 52c can be provided similar to first energy 52a. A characteristic of the waveform 52c, can include, for example, a first frequency and/or waveform, such as a rectangular waveform, or the like. Such a waveform 52c can be used to provide first energy 52a to power adapter 500. The power adapter 500 can then convert the first energy 52a to second energy 52b having a second frequency and/or waveform.

FIGS. 5D and 5E show waveforms 52d and 52e, respectively, that are examples of waveforms of second energy 52b (e.g., as input by the power adapter 500 to the electrode 59a, and applied by the implant 504 via output at the electrode 59b). Specifically, the waveform 52d is a rectified version of the waveform 52c of FIG. 5C (e.g., using envelope detection rectification). More specifically, the square wave bursts of the waveform 52c are rectified to produce the square waveform 52d, which effectively is a square waveform having a lower frequency than the square wave bursts of the waveform 52c. As another example, the waveform 52e of FIG. 5D can be produced using simple rectification of the waveform 52c. Specifically, the waveform 52e includes the positive components of the waveform 52c, and has removed the negative portions of the waveform 52c. In some instances, the frequency of the waveform 52e (e.g., of the second energy) can be similar or substantially equal or identical to the frequency of the waveform 52c (e.g., of the first energy).

FIG. 5F is a graph illustrating the relationship between charge per burst and frequency when applied transcutaneously to an individual, according to an embodiment. As shown in FIG. 5F, the predetermined frequency or range of frequencies (e.g., at which the first energy is output from the transmitter 502b) can include, for example, a frequency or range of frequencies in the range of approximately 10 kHz to 60 kHz. The predetermined frequency or range of frequencies can otherwise include a frequency or range of frequencies and the range of energy and/or charge at which the energy output from the transmitter 102 can be applied, such as to a body of a subject, without causing a response, or stimulation ("response"), such as a local motor response or sensation, in and by the body. For example, the predetermined frequency or range of frequencies and the amount of energy and/or charge can be chosen or determined to achieve a targeted response (labeled "Targeted response") as a function of frequency with respect to a magnitude of the applied energy. The magnitude of the applied energy can be specified, for example, such as in terms of a current magnitude, measured in Coulombs. As illustrated in FIG. 5F, as the frequency increases, the amount of energy and/or charge that can be applied to the individual without an undesirable local response can also increase. Line A illustrated in FIG. 5F is an example frequency at which the transmitter 502a of FIG. 5A can transmit the first energy 51a. Line B illustrated in FIG. 5F is an example frequency at which the transmitter 502b of FIG. 5B can transmit the first energy 52a to the power adapter 500. In some instances, when at higher frequencies, there can be a larger margin ("operational window") between the energy sufficient to result in a response of the targeted tissue near the implant and the energy sufficient to result in an undesirable local response under the skin electrodes.

While the transmitters 502a is described above as transmitting the first energy 51a having a relatively low frequency and the transmitter 502b is described above as transmitting the first energy 52a having a relatively high frequency, in some embodiments, a transmitter can be configured to transmit energy that includes any suitable combination of the energy 51a (e.g., the relatively low frequency) and the energy 52a (e.g., the relatively high frequency). In such implementations, the transmitter can transmit the energy in any suitable pattern, combination, sequence, interlaced or non-interlaced series, time-dependent bursts or pulses, random bursts or pulses, and/or the like. In some instances, the relatively low frequency energy can be configured to result in and/or otherwise cause a desirable local response such as, for example, increased blood flow or other desirable response within a region of the body adjacent and/or near the transmitter, while the relatively high frequency energy can be received by the power adapter and transmitted to the implant, as described above.

Figure 6A:
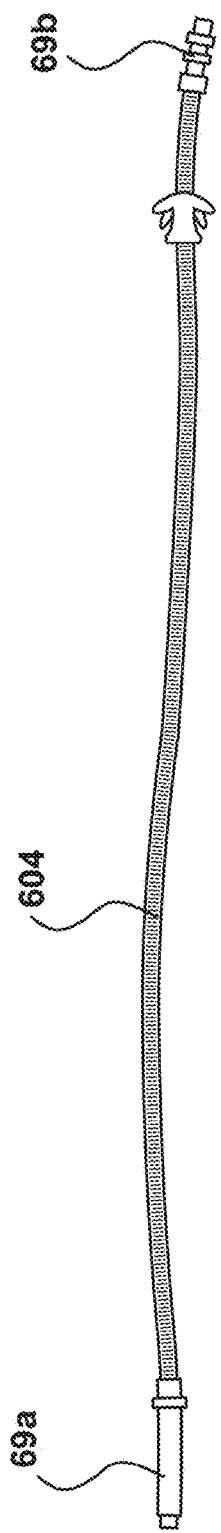
FIGS. 6A-6F depict various views of a power adapter and/or an implant, in accordance with an embodiment.
Figure 6B:
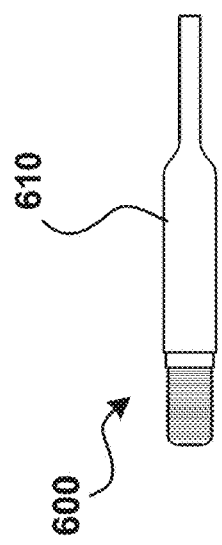
Figure 6C:
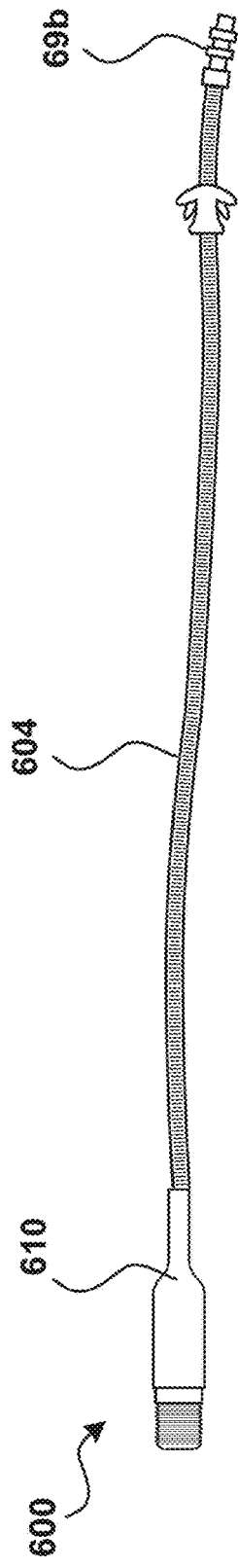

FIGS. 6A-6F depict various views of a power adapter 600 and/or an implant 604, in accordance with an embodiment. The power adapter 600 can be structurally and/or functionally similar to other power adapters (e.g., 100, 200, 300, and/or 500) shown and described herein. The implant 604 can be structurally and/or functionally similar to other implants (e.g., 104, 304, and/or 504) shown and described herein. For example, the implant 604 can include a pick-up electrode 69a and a stimulating electrode 69b, such as shown in FIG. 6A.

Figure 6D:
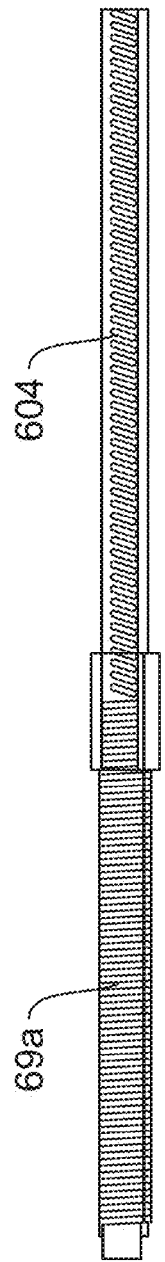
Figure 6E:
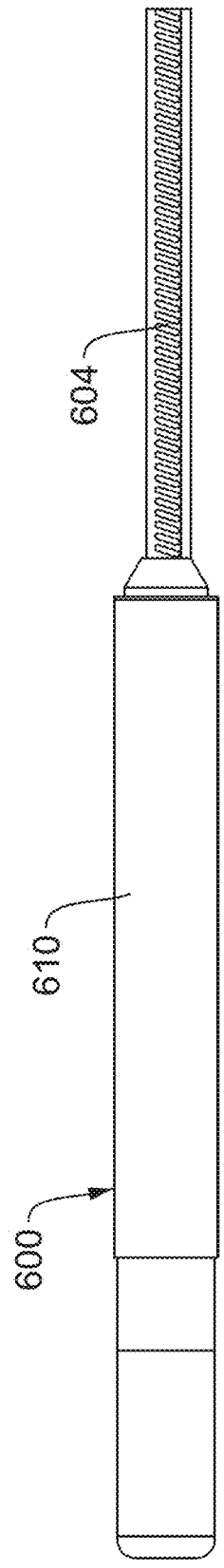
Figure 6F:
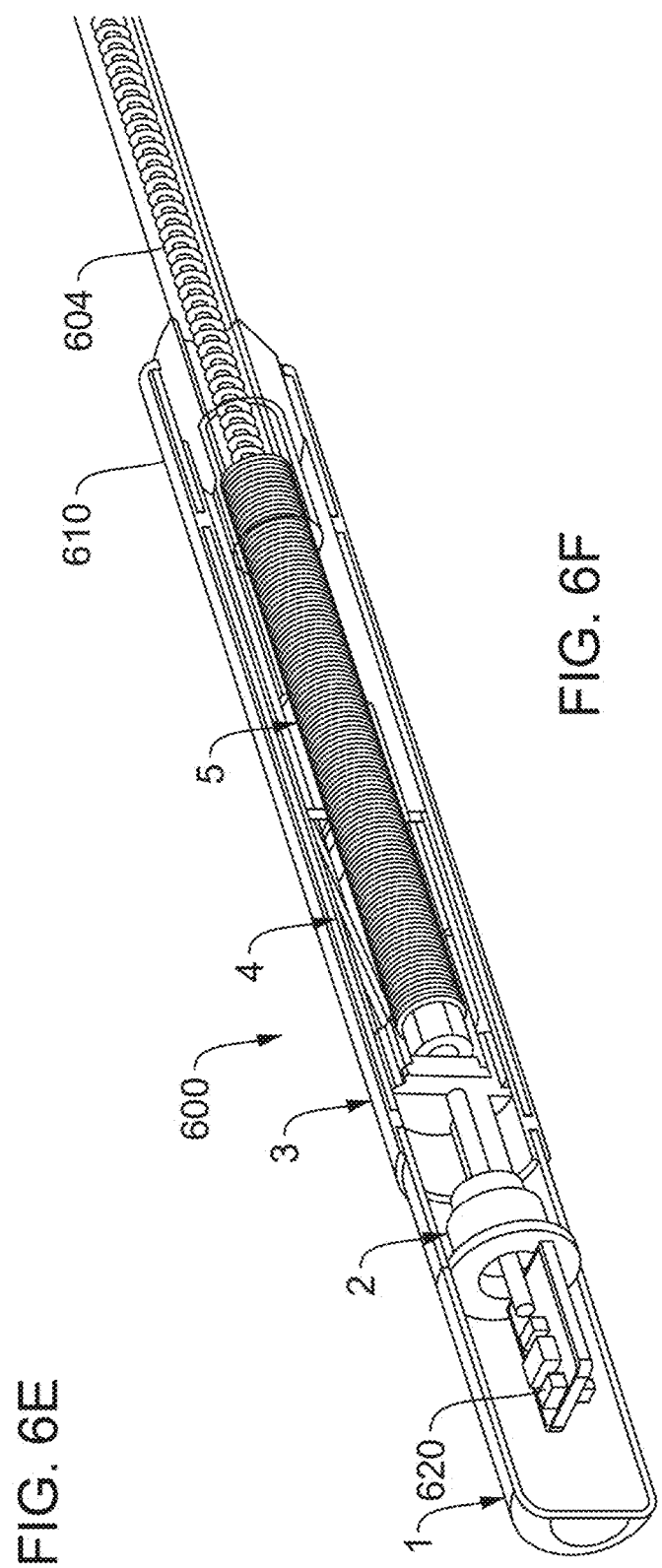

In some implementations, the housing 610 can be configured to be coupled, for example, to, on, and/or over implant 604, such that the housing 610 at least partially covers an end of implant 604, such as shown in FIGS. 6E and 6F. For example, the housing 610 can be configured to be coupled on and over implant 604 to at least partially cover (e.g., non-hermetically) one or more of the electrodes, such as a pick-up electrode, of the implant 604, as described herein. In this example, in covering one or more of the electrodes of the implant 604, the housing 610 can be configured to insulate (e.g., electrically insulate) the one or more (e.g., covered) electrodes from surrounding tissue (e.g., as in environment 101) when disposed in a body with implant 604. In some implementations, the one or more covered (e.g., by housing 610) electrodes of implant 604 can include, for example, a pick-up electrode. In some implementations, the housing 610 can be configured to be coupled to, on, and over implant 604 with a retainment force of approximately 6.5 Newtons (N).

The pick-up electrode 69a of the implant 604 is shown in FIG. 6D. As shown in FIG. 6E, the power adapter 600 can be attached on and over the pick-up electrode of the implant 604. As shown in FIG. 6F, circuit 620 can be at least partially disposed in the housing 610, where the housing 610 includes, for example, a housing (1), configured to function as a pick-up electrode of the power adapter 600. The housing 610 can be configured to hermetically seal the circuit 620 inside the housing (1). Further, as shown in FIG. 6F, the power adapter 600 can include a feed-through conductor (2) through which (converted) energy from the circuit 620 can be transferred to the stimulating electrode of the implant 604. Further, as shown in FIG. 6F, the power adapter 600 can include electrical conductors (4). The electrical conductors (4) can be, for example, press-fit against the pick-up electrode of the (5) of the implant 604. The housing 610 can include a housing configured to couple to the implant 604, and to fit over the pick-up electrode of the implant 604, upon coupling of the housing 610 to the implant 604. The housing 610 can include a silicone sleeve (3), to electrically insulate the pick-up electrode from surrounding tissue (e.g., when the housing 610 is coupled to the implant 604 and disposed in a body). The silicone sleeve (3) can be configured to provide a friction or retainment force to the coupling between the housing 610 and the implant 604 upon coupling of the housing 610 to the implant 604. For example, the silicone sleeve (3) can be configured to apply pressure and friction to the coupling or interface between the power adapter 600 and the implant 604 upon coupling of the housing 610 to the implant 604.

Figure 7A:
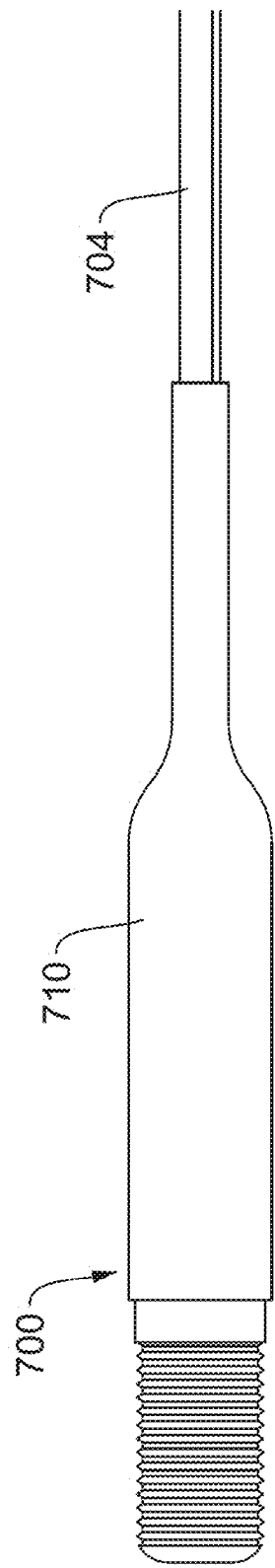
FIGS. 7A and 7B depict a side view and a partial cross-sectional perspective view, respectively, of a power adapter and an implant, in accordance with an embodiment.
Figure 7B:
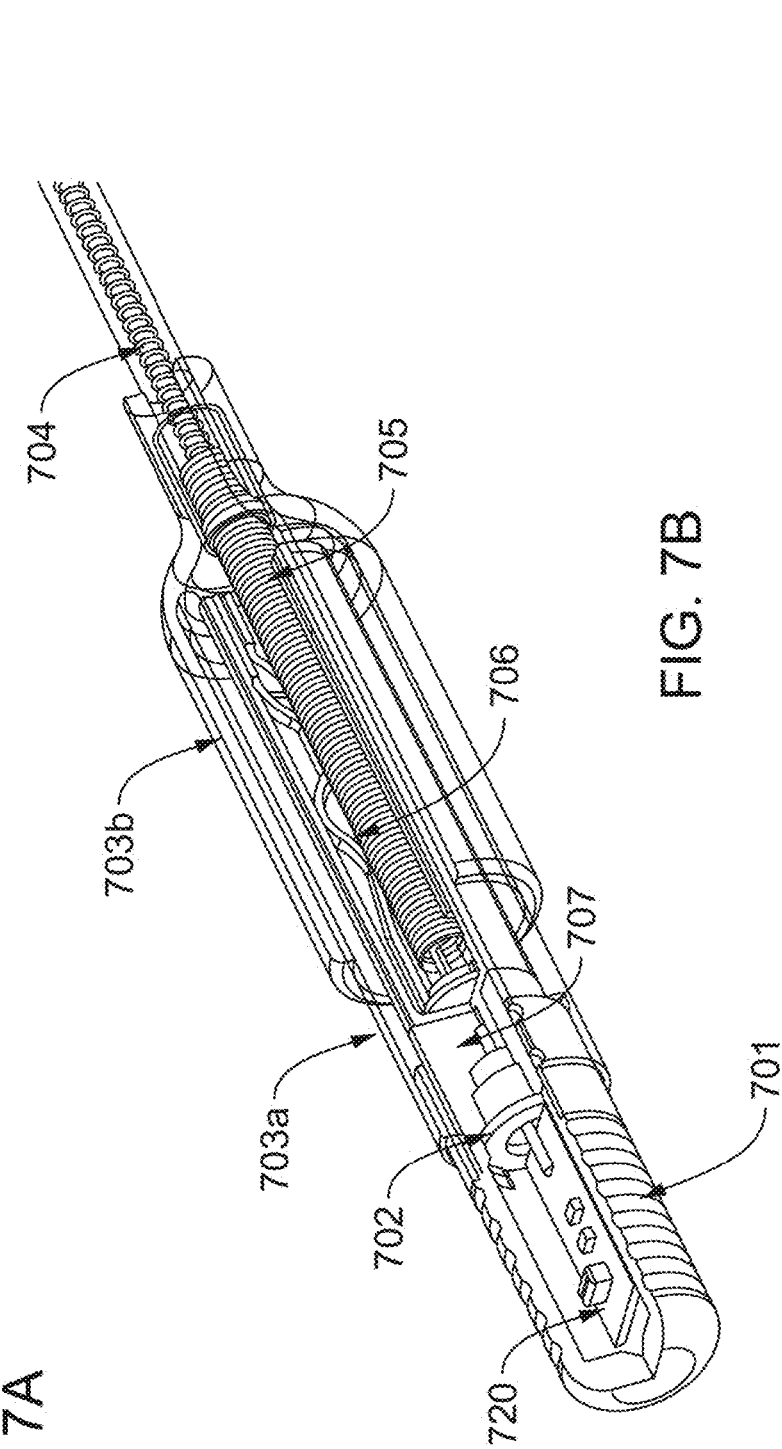

FIGS. 7A and 7B depict a side view and a partial cross-sectional view, respectively, of a power adapter 700 and a portion of an implant 704, in accordance with an embodiment. The power adapter 700 can be structurally and/or functionally similar to other power adapters (e.g., 100, 200, 300, 500, and/or 600) shown and described herein. The implant 704 can be structurally and/or functionally similar to other implants (e.g., 104, 304, 504, and/or 604) shown and described herein. For example, the implant 704 can include a pick-up electrode and a stimulating electrode (not shown), as described above with reference to the implant 604 of FIG. 6A.

In some implementations, a housing 710 of the power adapter 700 can be configured to be coupled, for example, to, on, and/or over implant 704, such that the housing 710 at least partially covers an end of implant 704, such as shown in FIGS. 7A and 7B. For example, the housing 710 can be configured to be coupled on and over implant 704 to at least partially cover (e.g., non-hermetically) one or more of the electrodes, such as a pick-up electrode, of the implant 704, as described herein. In this example, in covering one or more of the electrodes of the implant 704, the housing 710 can be configured to insulate (e.g., electrically insulate) the one or more (e.g., covered) electrodes from surrounding tissue (e.g., as in environment 101) when disposed in a body with implant 704. In some implementations, the one or more covered (e.g., by housing 710) electrodes of implant 704 can include, for example, a pick-up electrode. In some implementations, the housing 710 can be configured to be coupled to, on, and over implant 704 with a retainment force of approximately 6.5 Newtons (N).

As shown in FIG. 7B, the power adapter 700 can be attached on and over a pick-up electrode 705 of the implant 704. A circuit 720 can be at least partially disposed in the housing 710 and, in conjunction with the pick-up electrode 705, can be configured to function as a pick-up electrode of the power adapter 700. The housing 710 can be configured to hermetically seal the circuit 720 inside the housing 710. As shown, the housing 710 can include a first sleeve 703A and a second sleeve 703B. The first sleeve 703A can be, for example, a sleeve, cover, housing, etc. formed from any suitable material. For example, the first sleeve 703A can be formed from materials such as thermoplastic polyurethane (e.g., Tecothane), polyether ether ketone (PEEK), and/or the like. Similarly, the second sleeve 703B can be a sleeve, cover, housing, etc. formed from any suitable material (e.g., a material similar to or different from the material of the first sleeve 703A). For example, the second sleeve 703B can be formed from a material such as silicone and/or the like. In some embodiments, at least one of the first sleeve 703A and/or the second sleeve 703B can be configured to electrically insulate the pick-up electrode 705 from surrounding tissue (e.g., when the housing 710 is coupled to the implant 704 and disposed in a body). Further, the first sleeve 703A and the second sleeve 703B—alone or in combination—can be configured to provide a friction or retainment force to the coupling between the housing 710 and the implant 704. For example, the sleeve(s) 703A and/or 703B can be configured to apply pressure and friction to the coupling or interface between the power adapter 700 and the implant 704 upon coupling of the housing 710 to the implant 704.

As shown in FIG. 7B, the power adapter 700 can include a feed-through conductor 702 through which (converted) energy from the circuit 720 can be transferred to the stimulating electrode of the implant 704. The power adapter 700 can further include electrical conductors 706. The electrical conductors 706 can be, for example, press-fit against the pick-up electrode 705 of the implant 704. The electrical conductors 706 can be electrically connected to the feed-through conductor 702, thereby allowing the electrical conductors 706 to transmit electric power between the feed-through conductor 702 and the pick-up electrode 705 of the implant 704. A space 707 within the housing 710 at or around an interface between the feed-through conductor 702 and the electrical conductors 706 can be filed with epoxy and/or silicone and configured to electrically insulate the interface therebetween. Accordingly, the power adapter 700 can be structurally and/or functionally similar to the power adapter 600.

Figure 8A:
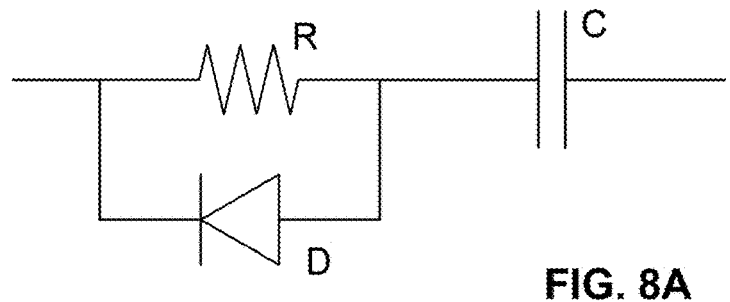
FIGS. 8A-8C are schematic diagrams depicting circuits of a power adapter, in accordance with various embodiments.

FIG. 8A is a schematic diagram depicting a circuit 821A of a power adapter, in accordance with an embodiment. The circuit 821A can be structurally and/or functionally similar to other circuits or a portion of other circuits (e.g., the circuit 221) described herein.

As shown, the circuit 821A includes a capacitor C (e.g., the capacitor 226) in series with a resistor R (e.g., the resistor 222), which is in parallel with a diode D (e.g., the diode 224). The diode D can include a rectifying diode. The capacitor C can include a DC blocking capacitor, as described above with respect to capacitor 226 in FIG. 2. In some embodiments, the capacitor C can be disposed on either side of the diode D. The diode D can be oriented in cathodic orientation or in anodic orientation. For example, in the cathodic orientation, when the circuit 821A is connected to an implant (e.g., the implant 104), a cathode of the diode D can be connected to the implant (e.g., at the electrode 19a). As another example, in the anodic orientation, when the circuit 821A is connected to an implant (e.g., the implant 104), an anode of the diode D can be connected to the implant (e.g., at the electrode 19a of the implant 104). The resistor R can be disposed in parallel to the diode to enable discharge of the capacitor C during positive phase of the pulse (e.g., second energy).

Figure 8B:
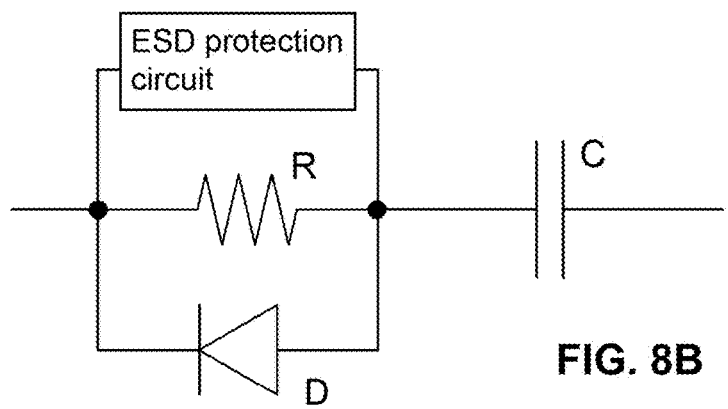
Figure 8C:
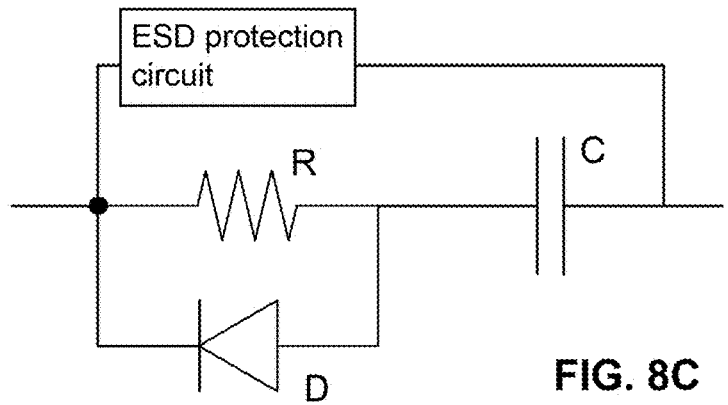

FIGS. 8B and 8C are schematic diagrams depicting individual circuits 821B and 821C, respectively, of a power adapter, in accordance with an embodiment. The circuits 821B and 821C can be configured to provide electrostatic discharge protection (ESD) via an ESD protection circuit. The circuits 821B and 821C can otherwise be structurally and/or functionally similar to other circuits or a portion of other circuits (e.g., the circuit 221) described herein.

As shown, the circuits 821B and 821C can include a capacitor C (e.g., the capacitor 226) in series with a resistor R (e.g., the resistor 222) and a diode D (e.g., the diode 224)—the resistor R is in parallel with the diode D. Moreover, each circuit 821B and 821C can include an electrostatic discharge (ESD) protection circuit, such as shown in FIG. 8B. For example, as shown in FIG. 8B, the circuit 821B can include the ESD protection circuit connected in parallel with the diode D (and the resistor R). Accordingly, the ESD protection circuit in the circuit 821B can be configured to provide protection over the diode D. As another example, as shown in FIG. 8C, the circuit 821C can include the ESD protection circuit connected in parallel with the diode D and the capacitor C (and the resistor R). In some implementations, the ESD protection circuit can include, for example, a diode such as a Zener diode, a transient volt suppressor (TVS) diode, bidirectional Zener diodes (e.g., two diodes connected in series front to front or back to back) and/or the like. The ESD protection circuit can be configured to reduce an exposure to risk of accidental electrostatic discharge such as during manufacturing and implantation, and further, reduces the need for other ESD protection.

Figure 9A:
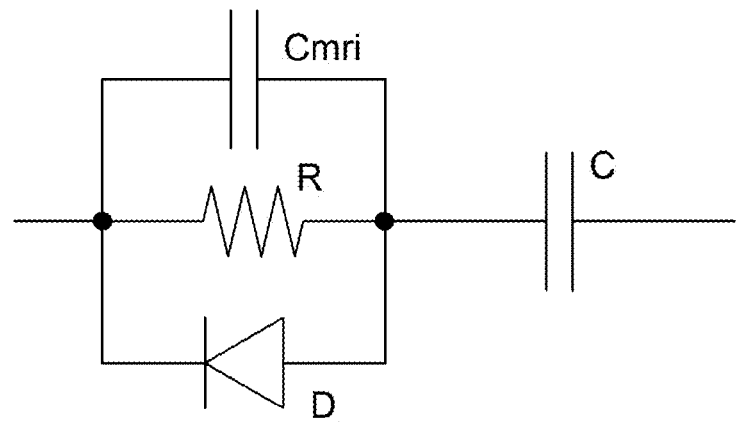
FIGS. 9A and 9B are schematic diagrams depicting circuits of a power adapter, in accordance with various embodiments.
Figure 9B:
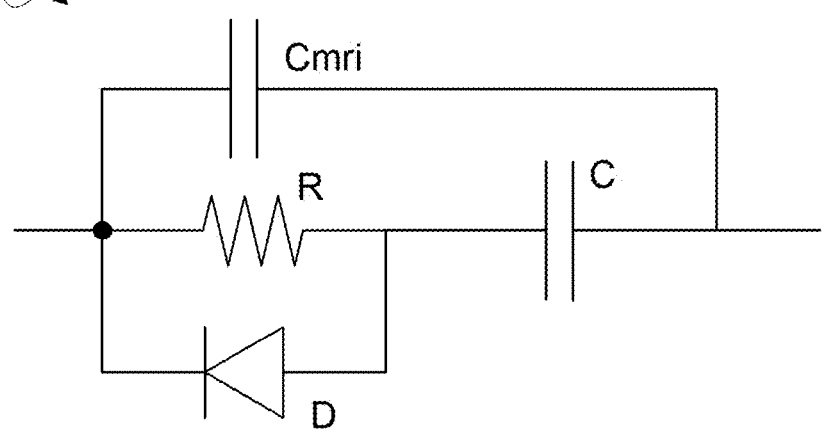

FIGS. 9A and 9B are schematic diagrams depicting individual circuits 921A and 921B, respectively, of a power adapter, in accordance with an embodiment. The circuits 921A and 921B can be structurally and/or functionally similar to other circuits or a portion of other circuits (e.g., the circuit 221) described herein.

As shown, each circuit 921A and 921B includes a capacitor C (e.g., the capacitor 226) in series with a resistor R (e.g., the resistor 222) and a diode D (e.g., the diode 224)—the resistor R is in parallel with the diode D. Moreover, each circuit 921 can include a capacitor Cmri configured to provide magnetic resonance imaging (MRI) protection. For example, as shown in FIG. 9A, the circuit 921A can include the capacitor Cmri connected in parallel with the diode D (and the resistor R). As another example, as shown in FIG. 9B, the circuit 921B can include the capacitor Cmri connected in parallel with the diode D and the capacitor C (and the resistor R). Accordingly, the capacitor Cmri, connected as such in either of the circuits 921A and 921B can be configured to provide, at low frequencies (50 kHz), relatively high impedance. Moreover, at higher frequencies (e.g., 64 MHz, 128 MHz) such as in MRI machines, the capacitor Cmri can be configured to provide low impedance and effectively will prevent rectification by effectively shorting (i.e., short-circuiting) the diode D. Thus, only non-rectified current will be delivered to the stimulating electrode (e.g., from either of the circuits 921A and 921B). Moreover, non-rectified current at 64 MHz or 128 MHz will not activate the nerve (unlike the rectified current), and will not cause any unintended stimulation and/or unpleasant sensation during the MRI procedure. For example, the capacitor Cmri be chosen to have a capacitance of approximately 100 picoFarads (pF), and, as such, can have an impedance, at 50 kHz of approximately 30,000 ohms; at 64 MHz=25 Ohm; and at 128 MHz=12 Ohm. The aforementioned frequencies are MRI frequencies (for 1.5 T and 3.0 T MRI machines respectively), which will bypass the rectifying circuit via the Cmri short circuit (e.g., 921A and 921B). Accordingly, at these frequencies, the circuits 921A and 921B are configured to not provide rectified pulses to the stimulating electrode of the implant (e.g., the implant 104).

Figure 10A:
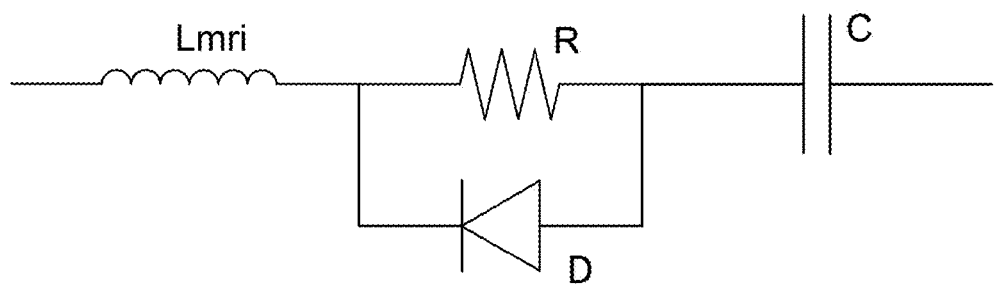
FIGS. 10A and 10B are a schematic diagrams depicting circuits of a power adapter, in accordance with various embodiments.
Figure 10B:
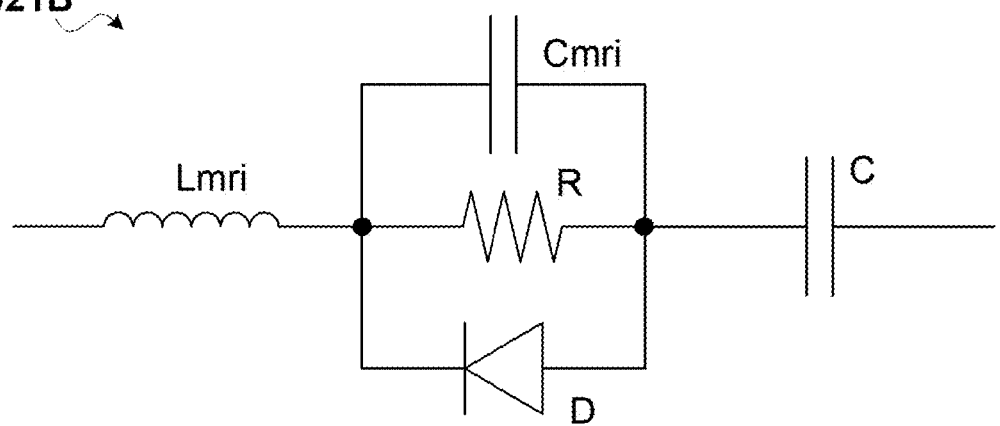

FIGS. 10A and 10B are schematic diagrams depicting individual circuits 1021A and 1020B, respectively, of a power adapter, in accordance with an embodiment. The circuits 1021A and 1021B can be structurally and/or functionally similar to other circuits or a portion of other circuits (e.g., the circuit 221) described herein.

As shown, each circuit 1021A and 1021B includes a capacitor C (e.g., the capacitor 226) in series with a resistor R (e.g., the resistor 222) and a diode D (e.g., diode 224)—the resistor R is in parallel with the diode D. As shown in FIG. 10A, the circuit 1021A can include an inductor Lmri disposed and connected in series with the rest of the circuit. Compared to adding a capacitor (e.g., Cmri) to the circuit (e.g., as shown in FIGS. 9A and 9B), the inductor Lmri can be configured to block higher frequencies, reduce current via the receiver, and can prevent undesired stimulation and also heating (e.g., of the power adapter 100 and/or the implant 104) due to the current flow. For example, the inductor Lmri be chosen to have an inductance of approximately 5 nanohenries (nH) to provide, at 50 kHz=2 Ohm; at 64 MHz=2 kOhm; at 128 MHz=4 kOhm. In some implementations, the inductor Lmri can include dimensions of approximately 2.5 mm×2.5 mm×3.8 mm. The aforementioned frequencies are MRI frequencies that will be blocked by the inductor, which is capable of blocking the MRI frequencies in the circuit 1021A (e.g., as described above with reference to the circuits 921A and 921B). Accordingly, at these frequencies, the circuit 1021A is configured to not provide pulses to the stimulating electrode of the implant (e.g., the implant 104), thereby providing protection to the patient when in an MRI machine.

While the circuit 1021A is shown in FIG. 10A as including the inductor Lmri as an alternative to the capacitor Cmri included in the circuits 921A and 921B, in some embodiments, a circuit can include both an inductor and a capacitor (e.g., a LC circuit). For example, as shown in FIG. 10B, the circuit 1021B includes a capacitor Cmri and an inductor Lmri, each of which can be configured to provide magnetic resonance imaging (MM) protection alone or in combination. As described above with reference to the circuit 1021A, the inductor Lmri in the circuit 1021B is connected in series with the rest of the circuit. Thus, at least one of the capacitor 1021A and/or the inductor 1021B can limit, prevent, and/or substantially prevent the circuit 1021B from providing pulses to the stimulating electrode of the implant (e.g., the implant 104), thereby providing protection to the patient when in an Mill machine.

Figure 11A:
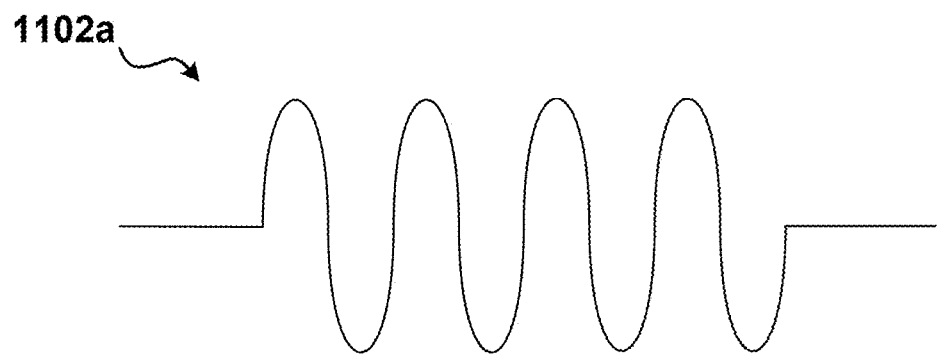
FIG. 11A depicts a non-rectified waveform (e.g., an alternating current waveform), in accordance with an embodiment.
Figure 11B:
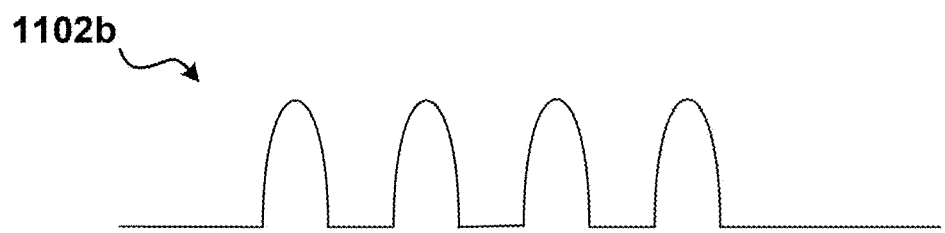
FIG. 11B depicts a one-way rectified waveform, in accordance with an embodiment.
Figure 11C:
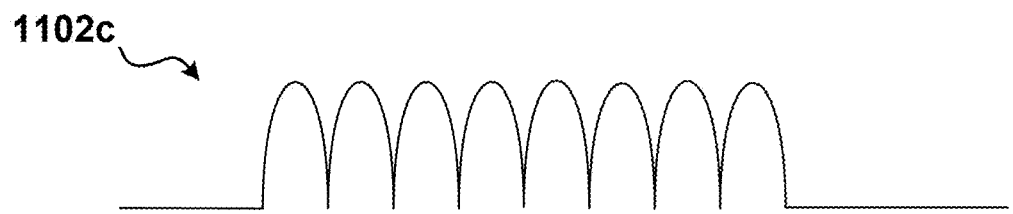
FIG. 11C depicts a two-way rectified waveform, in accordance with an embodiment.

FIGS. 11A-11C are waveforms illustrating potential waveforms used with respect to a power adapter, in accordance with an embodiment. Any of the power adapters described herein can be used with, can receive, can convert, and/or can output energy having any suitable characteristic or set of characteristics, which can include, for example, one or more characteristics associated with waveform. For example, FIG. 11A illustrates a waveform 1102a, in accordance with an embodiment. The waveform 1102a can be, for example, a non-rectified waveform associated with and/or otherwise having alternating current. As described in detail above, a transmitter such as those described herein can be configured to generate and provide energy (e.g., a first energy) to a power adapter. In some instances, the first energy can have a waveform similar to or substantially the same as the waveform 1102a shown, for example, in FIG. 11A.

The power adapters described in detail herein can be configured to receive a first energy and to convert and output a second energy. For example, the power adapters can include one or more circuits having any suitable components, as described in detail above with reference to specific embodiments. In some implementations, a power adapter can be configured to convert energy received from the transmitter (e.g., the first energy) to an energy (e.g., a second energy) having one or more different characteristics. For example, in some embodiments, the power adapter and/or at least a portion thereof can be configured to rectify the first energy received from the transmitter such that a second energy having a rectified waveform (e.g., a halfwave rectified waveform or a fullwave rectified waveform) is transferred to, for example, a pick-up electrode of an implant. In some instances, the rectification can be, for example, a one-way rectification (also referred to as halfwave-rectification). For example, FIG. 11B illustrates a waveform 1102*b* resulting from, for example, a one-way or halfwave rectification of the waveform 1102*a*. In other instances, the rectification can be, for example, a two-way rectification (also referred to as fullwave-rectification). For example, FIG. 11C illustrates a waveform 1102*c* resulting from, for example, a two-way or fullwave rectification of the waveform 1102*a*.

Figure 12A:
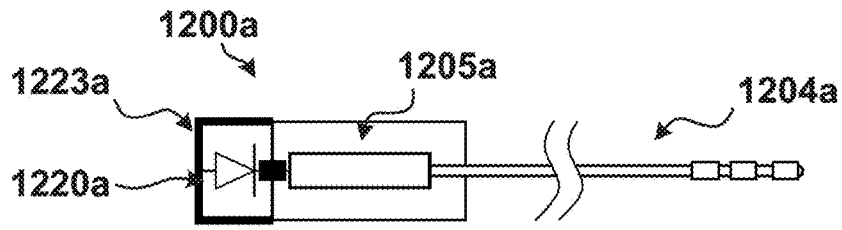
FIGS. 12A-12D are schematic diagrams depicting at least a portion of a power adapter, in accordance with various embodiments.

FIGS. 12A-12D are schematic diagrams depicting power adapters, in accordance with various embodiments. As described above with reference to FIGS. 11A-11C, in some implementations the power adapters described herein can be configured to rectify an energy transcutaneously received from a transmitter. More specifically, FIG. 12A illustrates a power adapter 1200*a* coupled to an implant 1204*a*. The power adapter 1200*a* and the implant 1204*a* can be similar in at least form and/or function to any of the power adapters and implants, respectively, described in detail herein. The power adapter 1200*a* can include a circuit 1220*a* and one or more electrodes 1223*a* that is/are configured to receive energy from the transmitter (e.g., as described above with reference to the electrode 123 and/or 223*a*). In the embodiment shown in FIG. 12A, the power adapter 1200*a* and/or the circuit 1220*a* can be configured to perform, for example, one-way or halfwave rectification on the energy (e.g., a first energy) received from the transmitter and can provide energy having the one-way of halfwave rectified waveform (e.g., shown in FIG. 11B) to a pick-up electrode 1205*a* of the implant 1204*a* (e.g., a second energy).

Figure 12B:
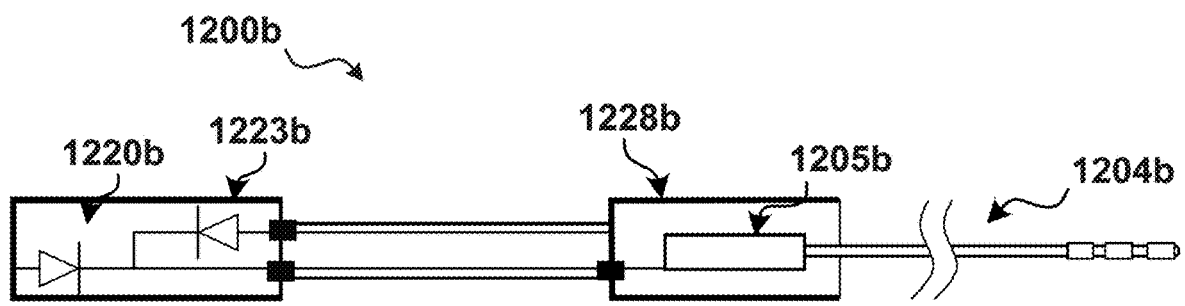

FIG. 12B illustrates a power adapter 1200*b* coupled to an implant 1204*b*, in accordance with an embodiment. The power adapter 1200*b* and the implant 1204*b* can be similar in at least form and/or function to any of the power adapters and implants, respectively, described in detail herein. As shown, the power adapter 1200*b* can include a circuit 1220*b*, one or more proximal electrodes 1223*b*, and a distal electrode 1228*b*. The electrodes 1223*b* and 1228*b* can be configured to receive energy from the transmitter, as described in detail above. In the embodiment shown in FIG. 12B, the power adapter 1200*b* can be configured as a lead or the like having the circuit 1220*b* disposed at or near the proximal end and the distal electrode 1228*b* disposed at or near the distal end. Moreover, the power adapter 1200*b* and/or the circuit 1220*b* can be configured to perform, for example, two-way or full-wave rectification on the energy (e.g., a first energy) received from the transmitter and can provide the two-way or fullwave rectified energy (e.g., a second energy) to a pick-up electrode of the implant 1204*b*. For example, in the example shown in FIG. 12B, the proximal electrode 1223*b* and the distal electrode 1228*b* can be in electrical communication with the transmitter and configured to transfer energy therebetween (e.g., via two electrical connections, wires, interconnects, etc.). In some embodiments, the circuit 1220*b* can include, for example, two or more diodes that can enable the power adapter 1200*b* and/or the circuit 1220*b* to perform the two-way or fullwave rectification on the energy received from the transmitter (e.g., a first energy). As such, the power adapter 1200*b* can be configured to provide two-way or fullwave rectified energy to a pick-up electrode 1205*b* of the implant 1204*b* (e.g., a second energy).

Figure 12C:
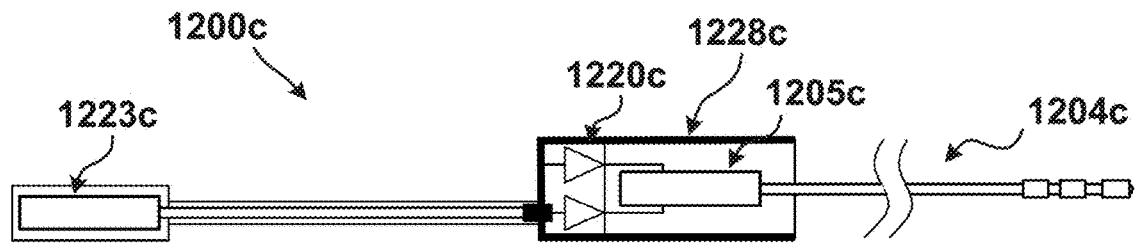

While the power adapter 1200*b* is shown and described as including the circuit 1220*b* at or near the proximal end and the distal electrode 1228*b* at or near the distal end, in other embodiments, a power adapter configured to perform two-way of fullwave rectification on energy received from a transmitter can have any suitable arrangement. For example, FIG. 12C illustrates a power adapter 1200*c* coupled to an implant 1204*c*, in accordance with an embodiment. In this example, the power adapter 1200*c* includes a circuit 1220*c* and a distal electrode 1228*c* at or near the distal end of the power adapter 1200*c* and a proximal electrode 1223*c* at or near the proximal end of the power adapter 1200*c*. In some implementations, the power adapter 1200*c* can be similar in at least function to the power adapter 1200*b* and, as such, can be configured to provide two-way of fullwave rectified energy to a pick-up electrode of the implant 1204*c*. In some embodiments, providing the circuit 1220*c* at or near the distal end of the power adapter 1200*c* can allow for a single electrical connection between the proximal electrode 1223*c* and the distal electrode 1228*c* (e.g., rather than two electrical connections, as shown in FIG. 12B).

Figure 12D:
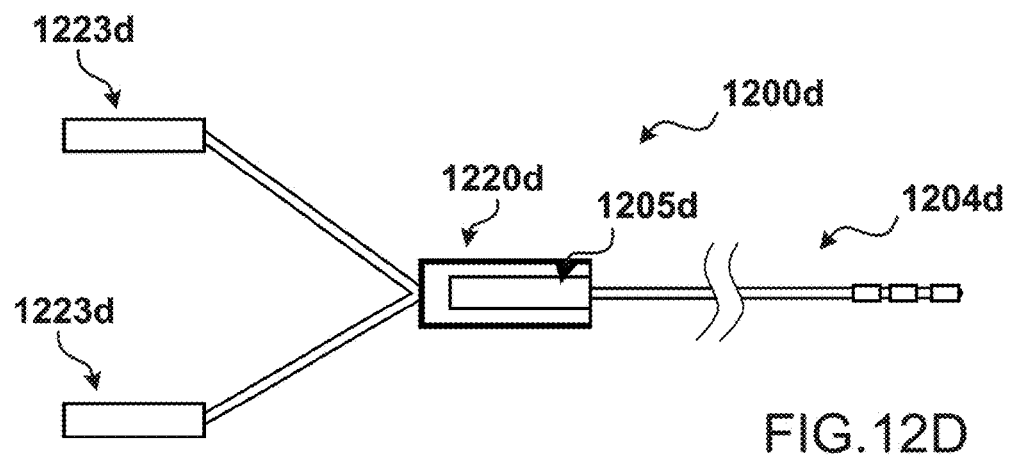

FIG. 12D illustrates a power adapter 1200*d* coupled to an implant 1204*d*, in accordance with an embodiment. In this example, the power adapter 1200*d* includes a circuit 1220*d* and a distal electrode (not shown in FIG. 12D) at or near the distal end of the power adapter 1200*d*, as described above with reference to the power adapter 1200*c* shown in FIG. 12C. In the example shown in FIG. 12D, the power adapter 1200*d* can include a pair of proximal electrodes 1223*d* at or near the proximal end of the power adapter 1200*d*. In some implementations, the power adapter 1200*d* can be similar in at least function to the power adapter 1200*b* and/or 1200*c* and, as such, can be configured to provide two-way rectified energy to a pick-up electrode of the implant 1204*d*. In some implementations, including various arrangements of one or more proximal electrodes (e.g., the proximal electrodes 1223*d*) can allow the power adapter 1200*d* to be used with transmitters having various shapes and/or sizes.

Figure 13:
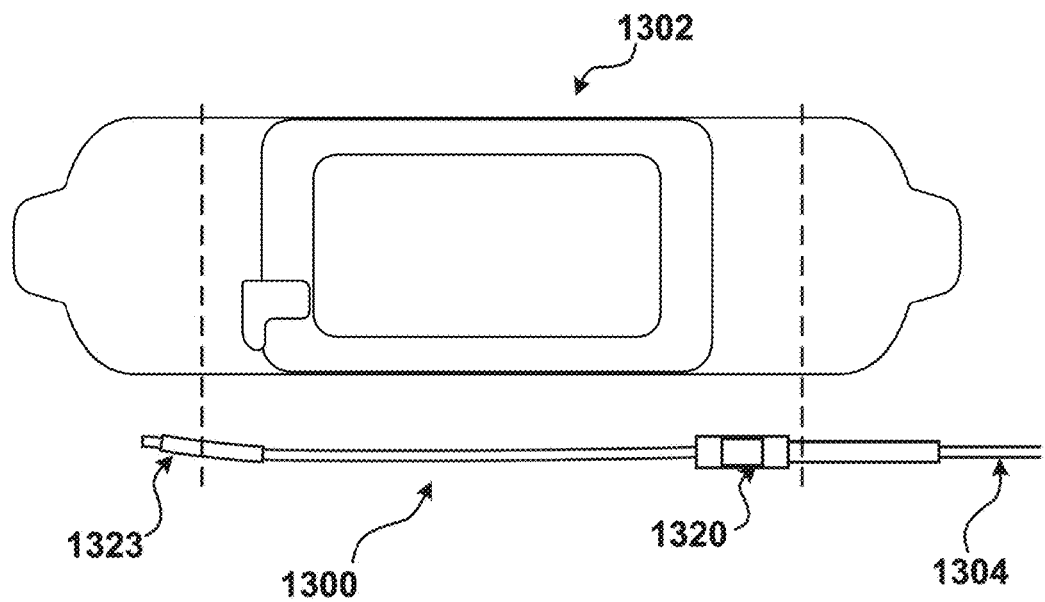
FIG. 13 depicts a transmitter, and a power adapter coupled to an implant, in accordance with an embodiment.

FIG. 13 illustrates a power adapter 1300 coupled to an implant 1304, and a transmitter 1302 configured to provide energy transcutaneously to the power adapter 1300, in accordance with an embodiment. As described above with reference to, for example, the power adapters 1200*b*, 1200*c*, and/or 1200*d*, the power adapter 1300 shown in FIG. 13 can be configured to perform two-way rectification on the energy received from a transmitter 1302. More particularly, the power adapter 1300 can be configured as a lead or the like that can be coupled to the implant 1304 as described in detail above. For example, the power adapter 1300 can be configured as a lead having a proximal electrode 1323 disposed at or near a proximal end of the lead and a circuit 1320 at or near a distal end of the lead.

In some embodiments, the lead can have a length of about 7.0 centimeters (cm). In other embodiments, the lead can be longer than 7.0 cm or can be shorter than 7.0 cm. In some embodiments, the length of the lead and/or power adapter 1300 can be at least partially based on a size and/or shape of the transmitter 1302 used therewith. For example, as shown in FIG. 13, the arrangement of the power adapter 1300 can be such that the proximal electrode 1323 is at least partially aligned with a first patch, a first side, and/or other suitable portion (e.g., a first portion) of the transmitter 1302 and the circuit 1320 and/or an electrode of the circuit 1320 (not shown in FIG. 13) is at least partially aligned with a second patch, second side, and/or other suitable portion (e.g., a second portion) of the transmitter 1302. As such, the power adapter 1300, the transmitter 1302, and a portion of the body disposed therebetween can form a circuit and/or at least a portion of a circuit, thereby allowing the power adapter 1300 to perform two-way rectification on the energy (e.g., a first energy) received from the transmitter 1302. Moreover, with the power adapter 1300 coupled to, for example, a pick-up electrode of the implant 1304, the power adapter 1300 can be configured to provide two-way rectified energy (e.g., a second energy) to the implant 1304, as described in detail herein.

Figure 14:
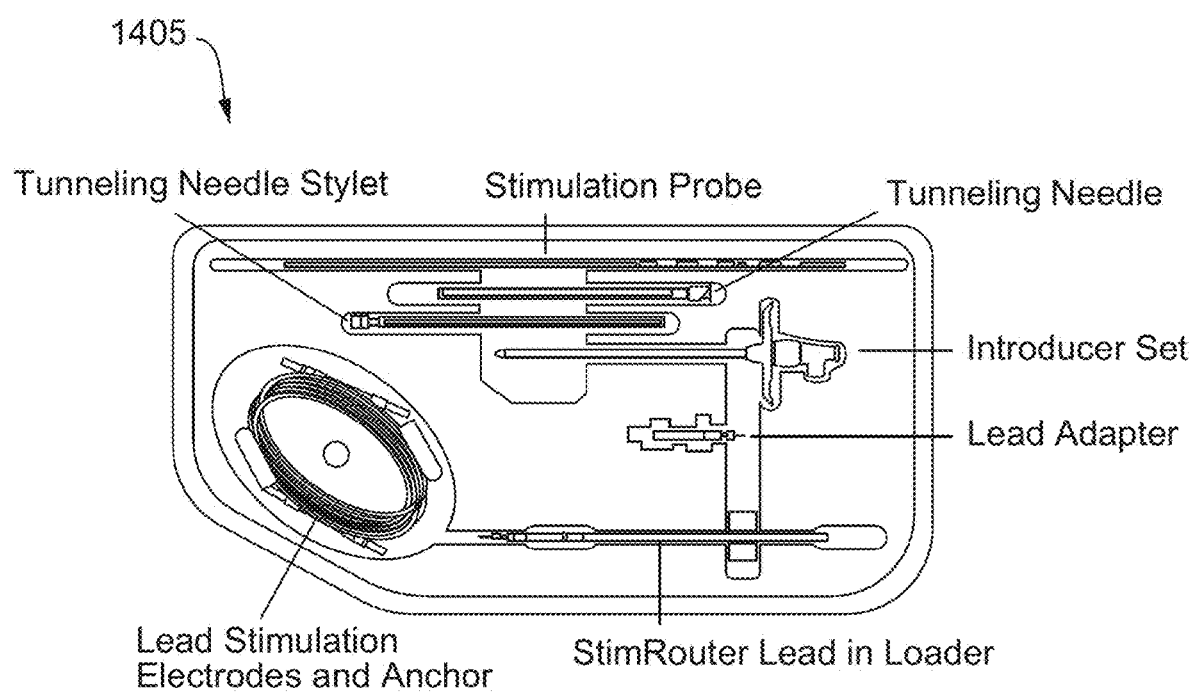
FIG. 14 is a schematic diagram depicting a kit including a power adapter and associated implements, in accordance with an embodiment.

FIG. 14 is a schematic diagram depicting a kit 1405 including an implant, in accordance with an embodiment. As shown, the kit 1405 can include a lead adapter (labeled "Lead Adapter"), an implant (labeled "StimRouter Lead in Loader"), a tunneling needle stylet, stimulation probes, a tunneling needle, an introducer set, and one or more lead stimulation electrodes, and an anchor. The kit 1405 can also include a power adapter (not shown in FIG. 14) that can be structurally and/or functionally similar to other power adapters (e.g., 100, 200, 300, 500, and/or 600) shown and described herein. The implant can be structurally and/or functionally similar to other implants (e.g., 104, 304, 504, and/or 604) shown and described herein. While the kit 1405 is shown as including seven or more discrete devices, other arrangements and/or configurations can include any number of devices and/or implements, in accordance with embodiments of the present disclosure.

The kit 1405 represents a tool set including various implements and tools by which to facilitate disposition of the implant in a body of a subject.

The lead adapter can include a lead adapter configured to couple the implant (e.g., 104, 304, 504, and/or 604) to a transmitter (e.g., transmitter 102) such as during an intraoperative implantation procedure. When provided as part of the kit 1405, the implant can include electrodes or probes, and be provided with an energy (e.g., signal, power) input end (e.g., at pick-up electrode) and an energy (e.g., signal, power) output end (e.g., at stimulating electrode, transducing end, sensing end), such as described herein. The implant can be provided in a loading or deployment device, or loader, configured to facilitate implantation of the implant in a body.

The loading or deployment device can be configured to maintain the implant in a sterile condition before and during end-use, and to reduce a risk of contamination during implantation of the implant (with the power adapter) in a body. The loading or deployment device can be configured to facilitate implantation of the implant (e.g., with the stimulating electrode end being the leading end).

The introducer set can include, for example, an incision-forming tool, a hollow tube (e.g., through which to dispose the power adapter and the implant in a body of a subject), and a seal. For example, the introducer set can include a trocar including an obturator, a tube such as a cannula, and a medical seal. The tunneling needle and the tunneling needle stylet can include a tunneling needle configured to facilitate access to a body, such for subsequent implantation of the implant (e.g., and the power adapter) in the body.

The anchor can include, for example, a silicon anchor. The anchor can otherwise include an anchor formed of any suitable material, such as a non-reactive or inert material, and the like. The anchor can be configured to fix the implant (e.g., along with the power adapter) in position in a body when disposed in the body. For example, the anchor can include a 4-pronged anchor configured to prevent or reduce lead migration after implantation. The kit 1405 can otherwise include any other suitable tool or implement for facilitating access to a body of a subject, and disposition (e.g., via implantation) of the power adapter and the implant in the body, in accordance with embodiments disclosed herein. For example, the kit 1405 can include tools and implements (provided and supplied in various conditions) such as listed in Table 1, below.

TABLE 1

Tools and Implements

| Components | Number included | Sterile |
|---|---|---|
| Implantable Lead (StimRouter Lead in Loader | 1 | Yes |
| Stimulation Probes | 2 | Yes |
| Stimulation Cables (yellow) | 2 | Yes |
| Introducer Set 9 Fr | 1 | Yes |
| Lead Adapter | 1 | Yes |
| Tunneling Needle | 1 | Yes |
| Tunneling Needle Stylet | 1 | Yes |
| Pack of 4 Gel Electrodes | 1 | No |
| Gel Electrode Cable (black) | 1 | No |
| Procedure Manual | 1 | No |

Detailed embodiments of the present disclosure have been disclosed herein or purposes of describing and illustrating claimed structures and methods that can be embodied in various forms, and are not intended to be exhaustive in any way, or limited to the disclosed embodiments. Many modifications and variations will be apparent without departing from the scope of the disclosed embodiments. The terminology used herein was chosen to best explain the principles of the one or more embodiments, practical applications, or technical improvements over current technologies, or to enable understanding of the embodiments disclosed herein. As described, details of well-known features and techniques can be omitted to avoid unnecessarily obscuring the embodiments of the present disclosure.

References in the specification to "one embodiment," "an embodiment," "an example embodiment," or the like, indicate that the embodiment described can include one or more particular features, structures, or characteristics, but it shall be understood that such particular features, structures, or characteristics may or may not be common to each and every disclosed embodiment disclosed herein. Moreover, such phrases do not necessarily refer to any one particular embodiment per se. As such, when one or more particular features, structures, or characteristics is described in connection with an embodiment, it is submitted that it is within the knowledge of those skilled in the art to affect such one or more features, structures, or characteristics in connection with other embodiments, where applicable, whether or not explicitly described.

Parameters, dimensions, materials, and configurations described herein are meant to be examples and that the actual parameters, dimensions, materials, and/or configurations will depend upon the specific application or applications for which the inventive teachings is/are used. It is, therefore, to be understood that the foregoing embodiments are presented by way of example only and that, within the scope of the appended claims and equivalents thereto; and that embodiments can be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

As used herein, the terms "about" and/or "approximately" when used in conjunction with values and/or ranges generally refer to those values and/or ranges near to a recited value and/or range. In some instances, the terms "about" and "approximately" may mean within ±10% of the recited value. For example, in some instances, "approximately a diameter of an instrument" may mean within ±10% of the length of the instrument. The terms "about" and "approximately" may be used interchangeably. Similarly, the term "substantially" when used in conjunction with physical and/or geometric feature(s), structure(s), characteristic(s), relationship(s), etc. is intended to convey that the feature(s), structure(s), characteristic(s), relationship(s), etc. so defined is/are nominally the feature(s), structure(s), characteristic(s), relationship(s), etc. As one example, a first quantity that is described as being "substantially equal" to a second quantity is intended to convey that, although equality may be desirable, some variance can occur. Such variance can result from manufacturing tolerances, limitations, approximations, and/or other practical considerations. Thus, the term "substantially".

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments described herein.

The specific configurations of the various components can also be varied. For example, the size and specific shape of the various components can be different from the embodiments shown, while still providing the functions as described herein. More specifically, the size and shape of the various components can be specifically selected for a desired or intended usage. Thus, it should be understood that the size, shape, and/or arrangement of the embodiments and/or components thereof can be adapted for a given use unless the context explicitly states otherwise.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

What is claimed:

1. A method, comprising:
receiving, transcutaneously at a first conductor of a power adapter and from an electrical pulse generator, a first energy having at least a first characteristic, the power adapter having a housing forming the first conductor, a second conductor disposed in the housing and electrically connected to an implantable electrical conductor coupled to the power adapter, and a sleeve disposed about a portion of the housing to electrically insulate the second conductor from the first energy outside of the sleeve;
converting, via a rectification circuit disposed in the housing, the first energy to a second energy having at least a second characteristic different from the first characteristic, the rectification circuit electrically connected between the first conductor and a second conductor; and
transferring, from the rectification circuit and to the implantable electrical conductor via the second conductor, the second energy such that a stimulating electrode of the implantable electrical conductor applies the second energy to a target nerve internal to a body.

2. The method of claim 1, wherein the first characteristic is a first frequency and the second characteristic is a second frequency different from the first frequency.

3. The method of claim 1, wherein the first characteristic is a first waveform and the second characteristic is a second waveform, the converting the first energy to the second energy includes one of halfwave rectification or fullwave rectification of the first waveform to generate the second energy having the second waveform.

4. The method of claim 1, wherein the first energy includes a plurality of bursts of energy, the plurality of bursts of energy including a combination of low frequency energy bursts and high frequency energy bursts, the low frequency energy bursts configured to result in a local response within a region in the body, the method further comprising:
receiving, at the rectification circuit and from the first conductor, the high frequency energy bursts;
converting, via the rectification circuit, the high frequency energy bursts to the second energy; and
transmitting, via the second conductor, the second energy to the implantable electrical conductor such that the stimulating electrode applies the second energy to the target nerve internal to the body and separated from the region in the body.

5. The method of claim 1, wherein the rectification circuit includes a rectifying diode, a direct current (DC) blocking capacitor, a resistor, and a receiving electrode.

6. The method of claim 1, wherein the rectification circuit includes a rectifying diode oriented such that the stimulating electrode applies cathodic stimulation to the target nerve.

7. The method of claim 1, wherein the rectification circuit incudes a rectifying diode and a capacitor in parallel with the rectifying diode, the method further comprising:
shorting, via the capacitor, the rectifying diode at about 64 MHz.

8. The method of claim 1, wherein the rectification circuit incudes a rectifying diode and a capacitor in parallel with the rectifying diode, the method further comprising:
shorting, via the capacitor, the rectifying diode at about 128 MHz.

9. The method of claim 1, wherein the rectification circuit incudes a rectifying diode, a capacitor in parallel with the rectifying diode, and an inductor in series with the rectifying diode.

10. The method of claim 1, wherein the rectification circuit includes a Zener diode for electrostatic discharge (ESD) protection.

11. A method, comprising:
receiving, via a housing of a power adapter, a first energy having a first set of characteristics from a power source outside of the body, the power adapter and an implantable device coupled to the power adapter being implanted in a body such that a stimulating electrode of the implantable device is proximate to a target nerve in the body;
converting, via a circuit of the power adapter disposed in the housing, the first energy to a second energy having a second set of characteristics different from the first set of characteristics, the circuit electrically connecting the housing to a pick-up electrode of the implantable device disposed in the housing, the power adapter having a sleeve disposed about a portion of the housing and electrically insulating the pick-up electrode from the first energy outside of the sleeve; and transferring the second energy from the circuit to the pick-up electrode of the implantable device such that the stimulating electrode of the implantable device applies the second energy to the target nerve.

12. The method of claim 11, wherein each of the first set of characteristics and the second set of characteristics includes a frequency characteristic, the first energy having a first frequency and the second energy having a second frequency different from the first frequency.

13. The method of claim 11, wherein the circuit is a rectification circuit, each of the first set of characteristics and the second set of characteristics including a waveform characteristic, the converting the first energy to the second energy includes one of halfwave rectification or fullwave rectification of the first energy having a first waveform to generate the second energy having a second waveform, different from the first waveform.

14. The method of claim 11, wherein the first energy includes a plurality of bursts of energy, the plurality of bursts of energy including a combination of low frequency energy bursts and high frequency energy bursts, the low frequency energy bursts configured to result in a local response within a region in the body, the method further comprising:
receiving, at the circuit and from the housing, the high frequency energy bursts;
converting, via the circuit, the high frequency energy bursts to the second energy; and
transmitting, from the circuit, the second energy to the pick-up electrode such that the stimulating electrode applies the second energy to the target nerve in the body and separated from the region in the body.

15. The method of claim 11, wherein the circuit includes a rectifying diode, a direct current (DC) blocking capacitor, a resistor, and a receiving electrode.

16. The method of claim 11, wherein the circuit includes a rectifying diode oriented such that the stimulating electrode applies cathodic stimulation to the target nerve.

17. The method of claim 11, wherein the circuit incudes a rectifying diode and a capacitor in parallel with the rectifying diode, the method further comprising:
shorting, via the capacitor, the rectifying diode at about 64 MHz.

18. The method of claim 11, wherein the circuit incudes a rectifying diode and a capacitor in parallel with the rectifying diode, the method further comprising:
shorting, via the capacitor, the rectifying diode at about 128 MHz.

19. The method of claim 11, wherein the circuit incudes a rectifying diode, a capacitor in parallel with the rectifying diode, and an inductor in series with the rectifying diode.

20. The method of claim 11, wherein the circuit includes a Zener diode for electrostatic discharge (ESD) protection.

21. A method, comprising:
receiving, transcutaneously via a first conductor of a power adapter, at least a portion of a first energy transmitted by an electrical pulse generator outside of the body, the power adapter and an implantable device coupled to the power adapter being implanted in a body, the power adapter having a housing forming the first conductor, a second conductor disposed in the housing and electrically connected to the implantable device, and a sleeve disposed about a portion of the housing to electrically insulate the second conductor from the first energy outside of the sleeve, the first energy including a combination of low frequency energy bursts and high frequency energy bursts, the low frequency energy bursts resulting in a local response within a region in the body between the electrical pulse generator and the power adapter;
converting, via a circuit disposed in the housing, the high frequency energy bursts of the first energy to a second energy different from the first energy; and
transferring the second energy from the second conductor to the implantable device such that a stimulating electrode of the implantable device applies the second energy to a target nerve internal to the body and separate from the region in the body.

22. The method of claim 21, wherein the circuit incudes a rectifying diode, a capacitor in parallel with the rectifying diode, and an inductor in series with the rectifying diode.

23. The method of claim 21, wherein the circuit includes a rectifying diode oriented such that the stimulating electrode applies cathodic stimulation to the target nerve.

24. The method of claim 21, wherein the circuit incudes a rectifying diode and a capacitor in parallel with the rectifying diode, the method further comprising:
shorting, via the capacitor, the rectifying diode at about 64 MHz.

25. The method of claim 21, wherein the circuit incudes a rectifying diode and a capacitor in parallel with the rectifying diode, the method further comprising:
shorting, via the capacitor, the rectifying diode at about 128 MHz.

26. The method of claim 21, wherein the circuit includes a rectifying diode, a direct current (DC) blocking capacitor, a resistor, and a receiving electrode.

27. The method of claim 21, wherein the circuit includes a Zener diode for electrostatic discharge (ESD) protection.

* * * * *

UNITED STATES PATENT AND TRADEMARK OFFICE
CERTIFICATE OF CORRECTION

PATENT NO. : 11,890,485 B2
APPLICATION NO. : 17/379220
DATED : February 6, 2024
INVENTOR(S) : Keith McBride et al.

It is certified that error appears in the above-identified patent and that said Letters Patent is hereby corrected as shown below:

In the Specification

In the Detailed Description:

Column 9, Line number 54: "quencies used with respect to Mill devices. The rectification"
Should read --quencies used with respect to MRI devices. The rectification--

Column 22, Line number 34: "when in an Mill machine."
Should read --when in an MRI machine.--

Signed and Sealed this
First Day of October, 2024

Katherine Kelly Vidal
*Director of the United States Patent and Trademark Office*